US006862480B2

(12) United States Patent
Cohen et al.

(10) Patent No.: US 6,862,480 B2
(45) Date of Patent: Mar. 1, 2005

(54) PELVIC DISORDER TREATMENT DEVICE

(75) Inventors: Ehud Cohen, Ganei Tikva (IL); Yossi Gross, Moshav Mazor (IL); Israel Nissenkorn, Ramat Aviv (IL)

(73) Assignee: Biocontrol Medical Ltd., Yehud (IL)

( * ) Notice: Subject to any disclaimer, the term of this patent is extended or adjusted under 35 U.S.C. 154(b) by 116 days.

(21) Appl. No.: 09/996,668

(22) Filed: Nov. 29, 2001

(65) Prior Publication Data

US 2003/0100930 A1 May 29, 2003

(51) Int. Cl.⁷ .............................................. A61N 1/08
(52) U.S. Cl. ......................... 607/41; 128/898; 600/30
(58) Field of Search .......................... 128/898; 600/30; 607/41, 115, 116, 117, 118, 138, 40

(56) References Cited

U.S. PATENT DOCUMENTS

| | | | |
|---|---|---|---|
| 3,628,538 A | 12/1971 | Vincent et al. | 128/422 |
| 3,640,284 A | 2/1972 | De Langis | 128/422 |
| 3,866,613 A | 2/1975 | Kenny et al. | 128/408 |
| 3,870,051 A | 3/1975 | Brindley | 128/422 |
| 3,926,178 A | 12/1975 | Feldzamen | 128/2 S |
| 3,941,136 A | 3/1976 | Bucalo | 128/422 |
| 3,983,865 A | 10/1976 | Shepard | 128/2.1 M |
| 3,983,881 A | 10/1976 | Wickham | 128/421 |
| 4,023,574 A | 5/1977 | Nemec | 128/420 |
| 4,106,511 A | 8/1978 | Erlandsson | 128/407 |
| 4,136,684 A | 1/1979 | Scattergood et al. | 128/2.1 M |
| 4,139,006 A | 2/1979 | Corey | 128/127 |
| 4,153,059 A | 5/1979 | Fravel et al. | 128/422 |
| 4,157,087 A | 6/1979 | Miller et al. | 128/741 |
| 4,165,750 A | 8/1979 | Aleev et al. | 128/422 |
| 4,177,819 A | 12/1979 | Kofsky et al. | 128/422 |
| 4,222,377 A | 9/1980 | Burton | 128/1 R |
| 4,290,420 A | 9/1981 | Manetta | 128/1 R |
| 4,406,288 A | 9/1983 | Horwinski et al. | 128/422 |

(List continued on next page.)

FOREIGN PATENT DOCUMENTS

| | | |
|---|---|---|
| WO | WO 00/19939 | 4/2000 |
| WO | WO 00/19940 | 4/2000 |

OTHER PUBLICATIONS

Fall, et al., "Electrical Stimulation in Interstitial Cystitis", Journal of Urology, 123(2), pp. 192–195, Feb. 1980.

(List continued on next page.)

*Primary Examiner*—Corrine McDermott
*Assistant Examiner*—Thomas J Sweet
(74) *Attorney, Agent, or Firm*—Ladas & Parry

(57) ABSTRACT

A device for treating a medical condition is provided, and a surgical procedure for implanting the device is disclosed. The device includes a sensor, which is adapted to generate a signal responsive to a state of a patient, and at least one electrode, which is adapted to be coupled to a pelvic site of the patient. A control unit is adapted to receive the signal, to analyze the signal so as to distinguish between an imminent stress incontinence event and an imminent urge event, and, responsive to analyzing the signal, to apply an electrical waveform to the at least one electrode. In various configurations, the device may be used alternatively or additionally to treat fecal incontinence, interstitial cystitis, chronic pelvic pain, or urine retention.

11 Claims, 18 Drawing Sheets

U.S. PATENT DOCUMENTS

| | | |
|---|---|---|
| 4,457,299 A | 7/1984 | Cornwell .................. 128/1 R |
| 4,492,233 A | 1/1985 | Petrofsky et al. ........... 128/421 |
| 4,515,167 A | 5/1985 | Hochman ................... 128/736 |
| 4,542,753 A | 9/1985 | Brenman et al. ........... 128/788 |
| 4,568,339 A | 2/1986 | Steer ......................... 604/329 |
| 4,571,749 A | 2/1986 | Fischell ..................... 623/14 |
| 4,580,578 A | 4/1986 | Barson ...................... 128/784 |
| 4,602,624 A | 7/1986 | Naples et al. |
| 4,607,639 A | 8/1986 | Tanagho et al. ........ 128/419 E |
| 4,628,942 A | 12/1986 | Sweeney et al. |
| 4,688,575 A | 8/1987 | DuVall ...................... 128/522 |
| 4,731,083 A | 3/1988 | Fischell ..................... 623/14 |
| 4,739,764 A | 4/1988 | Lue et al. ............... 128/419 R |
| 4,785,828 A | 11/1988 | Maurer ...................... 128/788 |
| 4,881,526 A | 11/1989 | Johnson et al. ............ 128/24.5 |
| 5,013,292 A * | 5/1991 | Lemay ....................... 600/30 |
| 5,285,781 A | 2/1994 | Brodard ..................... 607/59 |
| 5,291,902 A | 3/1994 | Carman ..................... 607/138 |
| 5,330,507 A | 7/1994 | Schwartz |
| 5,423,329 A | 6/1995 | Ergas ......................... 128/733 |
| 5,452,719 A | 9/1995 | Eisman et al. .............. 128/640 |
| 5,484,445 A | 1/1996 | Knuth ........................ 606/129 |
| 5,562,717 A | 10/1996 | Tippey et al. ................ 607/41 |
| 5,634,462 A | 6/1997 | Tyler et al. |
| 5,807,397 A | 9/1998 | Barreras ..................... 607/61 |
| 5,824,027 A | 10/1998 | Hoffer et al. |
| 5,833,595 A | 11/1998 | Lin |
| 5,927,282 A | 7/1999 | Lenker et al. .............. 128/885 |
| 6,002,964 A | 12/1999 | Feler et al. ................... 607/46 |
| 6,061,596 A | 5/2000 | Richmond et al. |
| 6,131,575 A | 10/2000 | Lenker et al. .............. 128/885 |
| 6,135,945 A | 10/2000 | Sultan ........................ 600/30 |
| 6,240,315 B1 | 5/2001 | Mo et al. ..................... 607/41 |
| 6,266,557 B1 | 7/2001 | Roe et al. |
| 6,266,564 B1 | 7/2001 | Hill et al. |
| 6,341,236 B1 | 1/2002 | Osorio et al. |
| 6,366,814 B1 | 4/2002 | Boveja et al. |
| 6,600,956 B2 | 7/2003 | Maschino et al. |
| 6,650,943 B1 | 11/2003 | Whitehurst et al. |
| 6,658,297 B2 | 12/2003 | Loeb |
| 6,659,936 B1 | 12/2003 | Furness et al. |
| 6,735,474 B1 | 5/2004 | Loeb et al. |
| 2002/0055761 A1 | 5/2002 | Mann et al. |
| 2003/0018365 A1 | 1/2003 | Loeb |
| 2003/0236557 A1 | 12/2003 | Whitehurst et al. |
| 2003/0236558 A1 | 12/2003 | Whitehurst et al. |
| 2004/0015204 A1 | 1/2004 | Whitehurst et al. |
| 2004/0015205 A1 | 1/2004 | Whitehurst et al. |
| 2004/0059392 A1 | 3/2004 | Parramon et al. |

OTHER PUBLICATIONS

Zermann, et al., "Sacral Nerve Stimulation for Pain Relief in Interstitial Cystitis", Urol. Int. 65(2), pp. 120–121, 2000.

Chai, et al., "Percutaneous Sacral Third Nerve Root Neurostimulation Improves Symptoms and Normalizes Urinary HB–EGF Levels and Antiproliferative Activity in Patients with Interstitial Cystitis", Urology, 55(5), pp. 643–646, May 2000.

P.D. O'Donnell ed., *Urinary Incontinence*, Chap. 26, 1997, Mosby Publishers, St. Louis, MI pp. 197–202.

Caraballo, et al., "Sacral Nerve Stimulation as a Treatment for urge Incontinence and Associated Pelvic Floor Disorders at a Pelvic Floor Center: A Follow–Up Study", Urology, 57(6 Suppl 1), p. 121, Jun. 2001.

U.S. Appl. No. 09/413,272, entitled: "Incontinence Treatment Device", filed Oct. 6, 1999.

Medtronic®'s InterStim Therapy for Urinary Control–Patient Stories, 1997, Nedtronic Inc., Spring Lake Park, MN, 2 pages. (http://webprod1.medtronic.com/neuro/interstim/4Bsize.html).

Summary of Safety and Effectiveness of Medtronic® Interstim® Sacral Nerve Stimulation (SNS)TM System, Sep. 1997, Medtronic Inc., Spring Lake Park, MN, 2 pages.

Medtronic®'s InterStim Therapy for Urinary..: for People with Bladder Control Problem, 1997, Medtronic Inc., Spring Lake Park, MN, 2 pages. (http://webprod1.medtronic.com/neuro/interstim/1types.html).

* cited by examiner

PELVIC DISORDER TREATMENT DEVICE

FIELD OF THE INVENTION

The present invention relates generally to electronic medical devices, and specifically to devices to relieve problems associated with urinary incontinence and other pelvic disorders.

BACKGROUND OF THE INVENTION

Urinary incontinence affects millions of people, causing discomfort and embarrassment, sometimes to the point of social isolation. In the United States, recent studies have shown that as many as 25 million persons, of whom approximately 85% are women, are affected by bladder control problems. Incontinence occurs in children and young adults, but the largest number affected are the elderly.

There are several major forms of incontinence:

Stress incontinence is an involuntary loss of urine while doing physical activities which put pressure on the abdomen. These activities include exercise, coughing, sneezing, laughing, lifting, or any body movement which puts pressure on the bladder. Stress incontinence is typically associated with either or both of the following anatomical conditions:

Urethral hypermobility—Weakness of or injury to pelvic floor muscles causes the bladder to descend during abdominal straining or pressure, allowing urine to leak out of the bladder. This is the more common source of stress incontinence.

Intrinsic sphincter deficiency—In this condition, the urethral musculature is unable to completely close the urethra or keep it closed during stress.

Urge incontinence is the sudden urgent need to pass urine, and is caused by a sudden bladder contraction that cannot be consciously inhibited. This type of incontinence is not uncommon among healthy people, and may be linked to disorders such as infections that produce muscle spasms in the bladder or urethra. Urge incontinence may also result from illnesses that affect the central nervous system.

Overflow incontinence refers to leakage of urine that occurs when the quantity of urine exceeds the bladder's holding capacity, typically as a result of a blockage in the lower urinary tract.

Reflex incontinence is the loss of urine when the person is unaware of the need to urinate. This condition may result from nerve dysfunction, or from a leak in the bladder, urethra, or ureter.

Of the major forms of incontinence listed above, the two most common are stress and urge. "Mixed incontinence" is a term used to describe the common phenomenon of the presence of stress and urge incontinence in the same patient.

A large variety of products and treatment methods are available for care of incontinence. Most patients suffering from mild to moderate incontinence use diapers or disposable absorbent pads. These products are not sufficiently absorbent to be effective in severe cases, are uncomfortable to wear, and can cause skin irritation as well as unpleasant odors. Other non-surgical products for controlling incontinence include urethral inserts (or plugs), externally worn adhesive patches, and drugs.

Exercise and behavioral training are also effective in some cases in rehabilitating pelvic muscles and thus reducing or resolving incontinence. Patients are taught to perform Kegel exercises to strengthen their pelvic muscles, which may be combined with electrical stimulation of the pelvic floor. Electromyographic biofeedback may also be provided to give the patients an indication as to the effectiveness of their muscular exertions. But retraining muscles is not possible or fully effective for most patients, particularly when there may be neurological damage or when other pathologies may be involved.

Medtronic Neurological, of Columbia Heights, Minn., produces a device known as Interstim, for treatment of urge incontinence. Interstim uses an implantable pulse generator, which is surgically implanted in the lower abdomen and wired to nerves near the sacrum (the bone at the base of the spine) in a major surgical procedure—sometimes six hours under general anesthesia. Electrical impulses are then transmitted continuously to a sacral nerve that controls urinary voiding. The continuous electrical stimulation of the nerve has been found to control urge incontinence in some patients.

Various surgical procedures have been developed for bladder neck suspension, primarily to control urethral hypermobility by elevating the bladder neck and urethra. These procedures typically use bone anchors and sutures or slings to support the bladder neck. The success rates for bladder neck suspension surgery in controlling urinary leakage are typically approximately 60%–80%, depending on the patient's condition, the surgeon's skill, and the procedure which is used. The disadvantages of this surgical technique are its high cost, the need for hospitalization and long recovery period, and the frequency of complications.

For serious cases of intrinsic sphincter deficiency, artificial urinary sphincters have been developed. For example, the AMS 600 urinary sphincter, produced by American Medical Systems Inc., of Minnetonka, Minn., includes a periurethral inflatable cuff, which is used to overcome urinary incontinence when the function of the natural sphincter is impaired. The cuff is coupled to a manually-operated pump and a pressure regulator chamber, which are implanted in a patient's body together with the cuff. The cuff is maintained at a constant pressure of 60–80 cm of water, which is generally higher than the bladder pressure. To urinate, the patient releases the pressure in the cuff. Aspects of this system are described in U.S. Pat. No. 4,222,377 to Burton, which is incorporated herein by reference.

This artificial sphincter has several shortcomings, however. The constant concentric pressure that the periurethral cuff exerts on the urethra can result in impaired blood supply to tissue in the area, leading to tissue atrophy, urethral erosion and infection. Furthermore, the constant pressure in the cuff is not always sufficient to overcome transient increases in bladder pressure that may result from straining, coughing, laughing or contraction of the detrusor muscle. In such cases, urine leakage may result.

U.S. Pat. Nos. 4,571,749 and 4,731,083 to Fischell, which are incorporated herein by reference, describe an artificial sphincter device whose pressure can vary in response to changes in abdominal or intravesical (bladder) pressure. The device includes a periurethral cuff, subdermic pump, pressure regulator, and hydraulic pressure sensor.

U.S. Pat. No. 3,628,538 to Vincent et al., which is incorporated herein by reference, describes apparatus for stimulating a muscle based on an electromyographic (EMG) signal sensed in the muscle. If the signal is greater than a predetermined threshold value, a stimulator circuit applies a voltage to electrodes adjacent to the muscle. The apparatus is said to be particularly useful in overcoming incontinence.

U.S. Pat. No. 6,135,945 to Sultan, which is incorporated herein by reference, describes apparatus for preventing uncontrolled discharge of urine from a patient's urethra. The apparatus includes an implantable pressure sensor for sensing intra-abdominal pressure, which generates a pressure signal in response to the sensed pressure. An actuating device is coupled to the pressure sensor, and generates an electrical signal in response to the pressure signal. A controller is coupled to the actuating device, and is configured to selectively compress the patient's urethra and thereby prevent incontinence.

Various types of electrodes have been proposed for applying electrical stimulation to pelvic muscles so as to prevent unwanted urine flow. For example, U.S. Pat. No. 5,562,717 to Tippey et al. describes electrodes that are placed on the body surface, typically in the areas of the perineum and the sacrum, and are electrically actuated to control incontinence. U.S. Pat. No. 4,785,828 to Maurer describes a vaginal plug having electrodes on an outer surface thereof. A pulse generator in the plug applies electrical pulses to the electrodes so as to constrict the patient's pelvic muscles and prevent urine flow. U.S. Pat. No. 4,153,059 to Fravel et al. describes an intra-anal electrode, to which repetitive electrical pulses are applied in order to control urinary incontinence. U.S. Pat. No. 4,106,511 to Erlandsson describes an electrical stimulator in the form of a plug for insertion into the vagina or the anus. U.S. Pat. No. 3,866,613 to Kenny et al. describes a pessary ring having two electrodes thereon, which are energized to control incontinence. U.S. Pat. No. 4,406,288 to Horwinski et al. describes apparatus for conditioning the pelvic floor musculature to reduce bladder contractility and relax the bladder, so as to prevent involuntary urinary loss. All of the above-mentioned patents are incorporated herein by reference.

U.S. Pat. No. 4,580,578 to Barson, which is incorporated herein by reference, describes a device for stimulating the sphincter muscles controlling the bladder. A supporting body is fitted into the patient's vulva between the labia, so that two electrodes attached to the supporting body contact the epidermal surface on either side of the external urethral orifice. Electrical impulses are applied to the electrodes to stimulate the region of the sphincter.

U.S. Pat. No. 4,607,639 to Tanagho et al., which is incorporated herein by reference, describes a method for controlling bladder function by nerve stimulation, typically of a sacral nerve. The anatomical location of at least one nerve controlling the muscles for the bladder and/or its sphincter is identified, and an electrode is placed on the nerve to selectively stimulate the nerve for continence and evacuation purposes.

U.S. Pat. No. 4,739,764 to Lue et al., which is incorporated herein by reference, describes a system for electrical stimulation of nerves in order to treat urinary incontinence, fecal incontinence, interstitial cystitis, and other pelvic pain syndromes.

U.S. Pat. No. 6,240,315 to Mo et al., which is incorporated herein by reference, describes incontinence treatment apparatus which includes a module for evaluating a recorded EMG signal.

U.S. Pat. No. 5,484,445 to Knuth, which is incorporated herein by reference, describes a system for anchoring a lead to the sacrum for purposes of long-term stimulation, typically for treatment of incontinence.

U.S. Pat. Nos. 5,927,282 and 6,131,575 to Lenker et al., which are incorporated herein by reference, describe removable external closures for the urethra as means for relieving or mitigating incontinence problems.

U.S. Pat. No. 6,002,964 to Feler et al., which is incorporated herein by reference, describe a method for managing chronic pelvic pain. The method includes techniques for positioning one or more stimulation leads within or about the sacrum to enable electrical energy to be applied to spinal nervous tissue, including nerve roots, in order to inhibit the transmission of pain signals.

An article by Fall et al., entitled, "Electrical stimulation in interstitial cystitis," Journal of Urology, 123(2), pp. 192–195, February, 1980, which is incorporated herein by reference, describes a study in which fourteen women with chronic interstitial cystitis were treated with long-term intravaginal or transcutaneous nerve stimulation. Clinical and urodynamic evaluations were performed after 6 months to 2 years. Improvement was not immediate, but required a considerable period of continuous, daily use of electrical stimulation.

An article by Zermann et al., entitled, "Sacral nerve stimulation for pain relief in interstitial cystitis," Urol. Int., 65(2), pp. 120–121, 2000, which is incorporated herein by reference, describes a case in which a 60-year-old woman was treated for severe interstitial cystitis pain using sacral nerve stimulation.

An article by Chai et al., entitled, "Percutaneous sacral third nerve root neurostimulation improves symptoms and normalizes urinary HB-EGF levels and antiproliferative activity in patients with interstitial cystitis," Urology, 55(5), pp. 643–646, May, 2000, which is incorporated herein by reference, notes: "A highly effective treatment for interstitial cystitis (IC) remains elusive. . . . Results suggest that permanent S3 PNS may be beneficial in treating IC."

An article by Caraballo et al., entitled, "Sacral nerve stimulation as a treatment for urge incontinence and associated pelvic floor disorders at a pelvic floor center: a follow-up study," Urology, 57(6 Suppl 1), p. 121, June, 2001, which is incorporated herein by reference, describes and presents the results of an additional study in which sacral nerve stimulation was applied in an effort to treat urinary incontinence.

PCT Patent Publication WO 00/19939, entitled, "Control of urge incontinence," which is assigned to the assignee of the present patent application and incorporated herein by reference, describes a device for treatment of urinary urge incontinence, in which imminent urge incontinence is sensed, and a pelvic nerve or muscle is stimulated to inhibit the flow.

PCT Patent Publication WO 00/19940, entitled, "Incontinence treatment device," which is assigned to the assignee of the present patent application and incorporated herein by reference, describes a device for treating urinary stress incontinence, in which imminent involuntary urine flow is sensed, and a pelvic nerve or muscle is stimulated to inhibit the flow.

A book entitled Urinary Incontinence, edited by P. O'Donnell, Mosby Publishers, 1997, which is incorporated herein by reference, describes clinical aspects relating to the diagnosis and treatment of urinary incontinence.

SUMMARY OF THE INVENTION

It is an object of some aspects of the present invention to provide devices and methods for treating mixed incontinence.

It is a further object of some aspects of the present invention to provide improved devices and methods for relieving pelvic pain.

It is yet a further object of some aspects of the present invention to provide improved devices and methods for treating fecal incontinence.

It is yet a further object of some aspects of the present invention to provide improved devices and methods for treating urine retention.

It is still a further object of some aspects of the present invention to provide improved methods for implanting pelvic electrical apparatus.

In preferred embodiments of the present invention, a device for treatment of both urinary stress incontinence and urge incontinence comprises a control unit, one or more electrodes coupled to the control unit, and one or more sensors, also coupled to the control unit. The electrodes are preferably implanted in the pelvic region of a patient so as to be in electrical contact with one or more of the muscles or nerves that are used in regulating urine flow from the bladder. The control unit is preferably implanted under the skin of the abdomen or genital region, and receives signals from the electrodes and/or from the sensors. Motion, pressure and/or electromyographic (EMG) signals conveyed by the electrodes or sensors are analyzed by the control unit, as described hereinbelow, in order to distinguish between signals indicative of urge incontinence and those indicative of stress incontinence. When the control unit determines that the signals are indicative of impending urge incontinence, it drives the electrodes to apply a signal having parameters configured to treat urge incontinence. When, however, the control unit determines that the signals are indicative of stress incontinence, it drives the electrodes to apply a signal having parameters that are configured to treat stress incontinence. As appropriate, the control unit may also configure the current applied by the electrodes so as to treat other disorders, such as fecal incontinence, interstitial cystitis, urine retention, or other sources of pelvic dysfunction, pain or discomfort.

It is to be appreciated that, in the context of the present patent application and in the claims, treatments described for inhibiting "imminent" conditions such as an event of stress incontinence which is expected to occur, may also be applied to inhibit a presently-occurring condition, such as involuntary voiding due to stress incontinence.

In addition, it is to be appreciated that although some preferred embodiments of the present invention are described herein with respect to treating urge incontinence, the scope of the present invention includes treating other urge "events" as well. For example, urge events such as urge frequency (the excessively frequent sensation of very imminent voiding, in patients who do not necessarily experience incontinence following such sensations) or neurogenic bladder conditions are preferably treated using identical protocols as those described herein for the treatment of urge incontinence, or protocols analogous to those described herein for the treatment of urge incontinence, mutatis mutandis.

Preferably, the control unit is programmed to distinguish between signals indicative of possible incontinence and other signals that do not warrant stimulation of the muscles. In particular, the control unit is preferably programmed to recognize signal patterns indicative of normal voiding, and, consequently, does not stimulate the muscles when such patterns occur.

Typically, devices in accordance with preferred embodiments of the present invention actuate the electrodes to treat urge or stress incontinence only when physiological or other signals indicate that such treatment is needed. At other times, stimulation is generally not applied. Implantation of the device provides reliable, typically long-term control of muscle function, and relieves incontinence or other pelvic disorders in a manner that is unobtrusive and minimizes inconvenience and discomfort of the patient. By contrast, many prior art electrical devices for treating pelvic disorders are not implanted or intended for long-term use, but are instead intended for temporary use, e.g., to train pelvic muscles via a device incorporated in a vaginal plug. These prior art devices are typically removed after a relatively short treatment period.

Numerous benefits are obtained, according to these embodiments, by actuating the electrodes only "on-demand," i.e., only when possible imminent stress or urge incontinence is detected. For example, muscle fatigue and nerve irritation—both phenomena being associated with continuous excitation—are typically reduced or eliminated according to these embodiments. Accordingly, power consumption is reduced, and battery life is thereby increased.

Preferably, the electrodes are implanted so as to stimulate muscles of the pelvic floor. Alternatively or additionally, one or more of the electrodes may be implanted in or adjacent to the detrusor muscle or in a position suitable for stimulating a nerve, such as the sacral nerve, as described in the above-mentioned U.S. Pat. No. 4,607,639, for example, or in one or more of the other references cited in the Background section of the present patent application.

In some preferred embodiments of the present invention, the one or more electrodes comprise a single electrode, which both receives the EMG signals and applies the stimulation waveform. Alternatively, separate sensing and stimulation electrodes may be used.

In some preferred embodiments of the present invention, the sensors comprise one or more mechanical sensors, such as pressure, force, motion or acceleration sensors, or an ultrasound transducer, which are preferably implanted on, in or in the vicinity of the bladder. These sensors preferably generate signals responsive to motion, to intravesical or abdominal pressure, or to urine volume in the bladder, and are thus indicative of possible imminent incontinence. The control unit processes the signals from the sensors in order to determine whether and what type of electrical stimulation should be applied.

In a preferred embodiment of the present invention, the patient herself instructs the control unit to initiate stimulation of the muscles. For example, the patient may input the instruction to the control unit by voluntarily tightening her abdominal muscles, which in turn causes measurable increases in abdominal pressure. Typically, this is done when the patient senses imminent urge incontinence. The control unit distinguishes the voluntary contraction from other sources of pressure changes responsive to the rate of change of the measured pressure. Alternatively or additionally, the control unit comprises an external input unit, such as a keypad, through which the patient enters instructions. For some applications, the patient is further enabled to indicate to the control unit that she feels imminent stress incontinence, e.g., shortly prior to sneezing.

In a preferred embodiment of the present invention, the processor is programmable after implantation of the device, most preferably by means of a wireless communications link, so that the strength and shape of the stimulation waveform and the response of the device to the electromyographic and/or other physiological signals can be adjusted in response to the patient's clinical characteristics and experience with the device. The wireless link can preferably also be used by the patient to turn the device on or off. Such methods of signal processing, programming and control, as well as other useful methods and apparatus, are described in U.S. patent application Ser. No. 09/413,272, entitled "Incontinence Treatment Device," which is assigned to the assignee of the present patent application and incorporated herein by reference.

There is therefore provided, in accordance with a preferred embodiment of the present invention, a device, including:

a sensor, which is adapted to generate a signal responsive to a state of a patient;

at least one electrode, which is adapted to be coupled to a pelvic site of the patient; and a control unit, which is adapted to receive the signal, to analyze the signal so as to distinguish between an imminent stress incontinence event and an imminent urge event, and, responsive to analyzing the signal, to apply an electrical waveform to the at least one electrode.

In a preferred embodiment, the at least one electrode includes a single electrode adapted to be coupled to the pelvic site, wherein the control unit is adapted to apply a first waveform to the single electrode responsive to determining that a stress incontinence event is imminent, and wherein the control unit is adapted to apply to the single electrode a second waveform, different from the first waveform, responsive to determining that an urge event is imminent.

Typically, the control unit is adapted to analyze the signal so as to distinguish between the imminent stress incontinence event and an imminent urge incontinence event. Alternatively or additionally, the control unit is adapted to analyze the signal so as to distinguish between the imminent stress incontinence event and an urge-frequency event.

In a preferred embodiment, the control unit is adapted to receive an input from the patient and to apply the waveform responsive to the input.

For some applications, the at least one electrode is adapted to be implanted so as to stimulate a nerve in the pelvic region of the patient. Alternatively or additionally, the at least one electrode is adapted to be implanted in contact with a pelvic muscle of the patient.

In a preferred embodiment, the at least one electrode includes:
- a first electrode, adapted to be coupled to a first pelvic site; and
- a second electrode, adapted to be coupled to a second pelvic site,
- wherein the control unit is adapted to apply a first waveform to the first electrode responsive to analyzing the signal and determining that a stress incontinence event is imminent, and wherein the control unit is adapted to apply to the second electrode a second waveform, different from the first waveform, responsive to determining that an urge event is imminent.

In this case, the first electrode is often adapted to be coupled to a pelvic muscle of the patient, while the second electrode is adapted to be coupled to a sacral nerve of the patient.

Preferably, the control unit is adapted to configure the waveform so as to stimulate a pelvic muscle to contract so as to inhibit involuntary urine flow through the patient's urethra. Typically, the control unit is adapted to configure the waveform so as to stimulate the pelvic muscle to contract responsive to analyzing the signal and determining that a stress incontinence event is imminent. Moreover, the control unit is preferably adapted to configure the waveform to have (a) a frequency component between about 40 and 50 Hz, (b) an amplitude between about 3 and 9 V, (c) a series of pulses having widths between about 0.05 and 1 ms, and/or a duration between about 0.2 and 1 second, responsive to determining that a stress incontinence event is imminent.

In a preferred embodiment, the control unit is adapted to configure the waveform so as to induce relaxation of a bladder muscle of the patient. Typically, the control unit is adapted to configure the waveform so as to induce the relaxation of the bladder muscle responsive to analyzing the signal and determining that an urge event is imminent. In this case, the control unit is preferably adapted to configure the waveform to have (a) a frequency component between about 5 and 15 Hz, (b) a duration less than about 10 minutes, (c) an amplitude between about 0.5 and 5 V, and/or (d) a series of pulses having widths between about 0.05 and 1 ms, responsive to determining that an urge event is imminent. For some applications, the control unit is adapted to configure the waveform to include a rise time lasting between about 1 second and 1 minute prior to attaining a designated waveform application voltage, responsive to determining that an urge event is imminent. Alternatively or additionally, the control unit is adapted to configure the waveform to include a decay time lasting between about 1 second and 1 minute prior to returning to a baseline voltage, responsive to determining that an urge event is imminent.

In a preferred embodiment, the control unit is adapted to configure the waveform to have a duty cycle between about 5% and 15%, responsive to determining that an urge event is imminent.

For some applications, the sensor includes a sensing electrode adapted to sense electrical activity of a bladder muscle of the patient. Preferably, but not necessarily, the at least one electrode includes the sensing electrode, and the control unit is adapted to apply the waveform to the sensing electrode responsive to analyzing the signal.

Typically, the sensor includes a pressure sensor, and the control unit is adapted to analyze a rate of change of the received signal, to identify the imminent stress incontinence event responsive to a relatively high rate of change of the received signal, and to identify the imminent urge event responsive to a relatively low rate of change of the received signal. In a preferred embodiment, the sensor is adapted to be implanted at an abdominal site of the patient, and the sensor is adapted to generate the signal with a relatively low rate of change responsive to voluntary contraction by the patient of abdominal musculature of the patient.

In a preferred application, the control unit is adapted to evaluate the imminence of the urge event responsive to an amount of time elapsed since the patient last voided.

Preferably, the sensor is adapted to be coupled to the patient's bladder, and includes a pressure sensor, an acceleration sensor, and/or an ultrasound transducer.

There is also provided, in accordance with a preferred embodiment of the present invention, a device, including:
- a first sensor, which is adapted to be coupled to a bladder site of a patient and to generate a first signal, responsive to a pressure in the bladder;
- a second sensor, which is adapted to be coupled to an abdominal site of the patient and to generate a second signal, responsive to an overall pressure in the abdomen;
- at least one electrode, which is adapted to be coupled to a pelvic site of the patient; and
- a control unit, which is adapted to receive the first and second signals, analyze the signals so as to distinguish between two conditions of the patient, and apply an electrical waveform to the at least one electrode, responsive to analyzing the signals.

Preferably, the first sensor includes a first pressure sensor, and wherein the second sensor includes a second pressure sensor.

In a preferred embodiment, the control unit is adapted to: (a) analyze the first and second signals so as to detect a characteristic in the first signal and a characteristic in the second signal, (b) identify whether the characteristic in the first signal is a significant change thereof and whether the characteristic in the second signal is a significant change thereof that generally corresponds in time to the change in the first signal, and (c) configure the waveform responsive to step (b).

Alternatively or additionally, the control unit is adapted to: (a) analyze the first and second signals so as to detect a characteristic in the first signal and a characteristic in the second signal, (b) identify whether the characteristic in the first signal is a significant change thereof and whether the characteristic in the second signal is a significant change thereof that generally corresponds in time to the change in the first signal, (c) apply a first waveform to the at least one electrode if the analysis identifies the change in the first signal as generally corresponding in time to the change in the second signal, and (d) apply to the at least one electrode a second waveform, different from the first waveform, if the analysis identifies the change in the first signal as not generally corresponding in time to the change in the second signal. In this case, the control unit is preferably adapted to configure the first waveform for treatment of stress incontinence of the patient, and wherein the control unit is adapted to configure the second waveform for treatment of an urge disorder of the patient.

There is further provided, in accordance with a preferred embodiment of the present invention, a device, including:

a sensor, which is adapted to generate a signal responsive to a state of a patient;

at least one electrode, which is adapted to be coupled to a pelvic site of the patient; and a control unit, which is adapted to receive the signal, to analyze the signal so as to determine a likelihood of imminent fecal incontinence, and, responsive to analyzing the signal, to apply an electrical waveform to the at least one electrode.

Preferably, the control unit is adapted to configure the waveform so as to stimulate an anal sphincter muscle to contract. Alternatively or additionally, the at least one electrode is adapted to be implanted so as to stimulate a nerve in the pelvic region of the patient. In a preferred embodiment, the at least one electrode is adapted to be implanted in contact with a pelvic muscle of the patient.

The control unit is preferably adapted to configure the waveform to have (a) a frequency component between about 40 and 50 Hz, (b) an amplitude between about 3 and 9 V, (c) a series of pulses having widths between about 0.05 and 1 ms, and/or (d) a duration between about 1 and 20 seconds.

Preferably, the at least one electrode includes a single monopolar electrode and/or at least one electrode includes a pair of bipolar electrodes. The at least one electrode typically includes a flexible intramuscular electrode.

In a preferred embodiment, the at least one electrode and the control unit are adapted to be implanted in the body of the patient.

In a preferred embodiment, the control unit is adapted to receive an input from the patient and to apply the waveform responsive to the input.

For some applications, the control unit is adapted to analyze the signal so as to distinguish between: (a) a first signal, indicative of imminent fecal incontinence, and (b) a second signal, indicative of voluntary voiding by the patient. For example, the control unit may be adapted to distinguish between the first and second signals responsive to a rate of change of the signal generated by the sensor. Alternatively or additionally, the control unit is adapted to gather information regarding the signal over an extended period and to analyze the information to find a pattern characteristic of the patient, for use in determining when imminent fecal incontinence is likely. In this case, the control unit is typically adapted to associate with the pattern a time-varying threshold to which a level of the signal is compared.

Typically, the sensor is adapted to be implanted at a pelvic location of the patient, and includes a pressure sensor, an acceleration sensor, an ultrasound transducer, and/or a sensing electrode. In a preferred embodiment, the sensor includes the at least one electrode.

For some applications, the sensor is adapted to generate the signal responsive to a level of filling of the rectum of the patient, and the control unit is adapted to apply the waveform to the at least one electrode responsive to the signal. In this case, the sensor typically includes a pressure sensor. Preferably, the control unit is adapted to increase a parameter of the waveform responsive to a level of the signal. Further preferably, the control unit is adapted to configure the waveform to be such as to induce afferent signaling in the patient, e.g., to be such as to induce in the patient afferent signaling of a form which induces a conscious sensation of rectal filling. In this latter case, the control unit is typically adapted to configure the waveform to be such as to induce in the patient afferent signaling of a form which induces a conscious sensation of rectal filling and an urge to voluntarily contract an anal sphincter muscle of the patient. Alternatively or additionally, the control unit is adapted to configure the waveform to be such as to induce afferent signaling in the patient of a form that induces contraction of a smooth muscle in a pelvic region of the patient and inhibits fecal incontinence.

There is yet further provided, in accordance with a preferred embodiment of the present invention, a device, including:

at least one electrode, which is adapted to be coupled to a pelvic muscle of a patient; and a control unit, which is adapted to drive the at least one electrode to apply to the muscle an electrical waveform configured to reduce patient pain due to interstitial cystitis.

For some applications, the control unit is adapted to receive an input from the patient and to apply the waveform responsive to the input. Alternatively or additionally, the control unit is adapted to drive the at least one electrode responsive to an amount of time elapsed since the patient last voided.

The control unit is typically adapted to configure the waveform so as to induce relaxation of a bladder muscle of the patient.

In a preferred embodiment, the control unit is adapted to configure the waveform to have (a) a frequency component between about 5 and 15 Hz, (b) an amplitude between about 1 and 4 V, (c) a series of pulses having widths between about 0.05 and 0.2 ms, and/or (d) a duration of about 10–30 minutes. Alternatively or additionally, the control unit is adapted to configure the waveform to include a rise time lasting between about 1 second and 3 minutes prior to attaining a designated waveform application voltage. Further alternatively or additionally, the control unit is adapted to configure the waveform to include a decay time lasting between about 1 second and 3 minutes, prior to returning to a baseline voltage.

For some applications, the control unit is adapted to configure the waveform to have a duty cycle between about 5% and 15%.

There is still further provided, in accordance with a preferred embodiment of the present invention, a device, including:

a sensor, which is adapted to generate a signal responsive to a state of a patient;

at least one electrode, which is adapted to be coupled to an anatomical site of the patient; and a control unit, which is adapted to receive the signal, to analyze the signal so as to determine a likelihood of imminent patient pain due to interstitial cystitis, and, responsive to analyzing the signal, to apply to the at least one electrode an electrical waveform configured to reduce patient pain due to interstitial cystitis.

For some applications, the sensor includes a sensing electrode adapted to sense electrical activity of a bladder muscle of the patient.

Alternatively or additionally, the control unit is adapted to evaluate the imminence of the interstitial cystitis responsive to an amount of time elapsed since the patient last voided.

In a preferred embodiment, the control unit is adapted to receive an indication of a fill level of the patient's bladder and to inhibit application of the electrical waveform when the fill level of the bladder is low.

Preferably, the control unit is adapted to analyze the signal so as to distinguish between: (a) a first signal, indicative of imminent interstitial cystitis, and (b) a second signal, indicative of voluntary voiding by the patient. For example, the control unit may be adapted to distinguish between the first and second signals responsive to a rate of change of the signal generated by the sensor. Alternatively or additionally, the control unit is adapted to gather information regarding the signal over an extended period and to analyze the information to find a pattern characteristic of the patient, for use in determining when imminent interstitial cystitis is likely. In this case, the control unit is preferably adapted to associate with the pattern a time-varying threshold to which a level of the signal is compared.

In a preferred embodiment, the sensor includes a pressure sensor, and the control unit is adapted to analyze a rate of change of the received signal, and to identify the imminent interstitial cystitis responsive to a low rate of change of the received signal.

In a preferred application, the sensor is adapted to be implanted at an abdominal site of the patient, and the sensor is adapted to generate the signal with a low rate of change responsive to voluntary contraction by the patient of abdominal musculature of the patient.

Typically, but not necessarily, the sensor is adapted to be coupled to the patient's bladder, and comprises a pressure sensor, an acceleration sensor, and/or an ultrasound transducer.

Preferably, the at least one electrode and the control unit are adapted to be implanted in the body of the patient. In this case, the at least one electrode is adapted to be implanted so as to stimulate a nerve in the pelvic region of the patient. Alternatively or additionally, the at least one electrode is adapted to be implanted in contact with a pelvic muscle of the patient.

There is additionally provided, in accordance with a preferred embodiment of the present invention, a device, including:

at least one electrode, which is adapted to be coupled to a pelvic muscle of a patient; and a control unit, which is adapted to drive the at least one electrode to apply to the muscle an electrical waveform configured to reduce patient pelvic pain.

There is still additionally provided, in accordance with a preferred embodiment of the present invention, a device, including:

a sensor, which is adapted to generate a signal responsive to a state of a patient;

at least one electrode, which is adapted to be coupled to an anatomical site of the patient; and a control unit, which is adapted to receive the signal, to analyze the signal so as to determine a likelihood of patient pelvic pain, and, responsive to analyzing the signal, to apply to the at least one electrode an electrical waveform configured to reduce the patient pelvic pain.

These devices for reducing patient pelvic pain are preferably configured to be similar to the devices for treating interstitial cystitis described herein.

There is yet additionally provided, in accordance with a preferred embodiment of the present invention, a device, including:

a sensor, which is adapted to generate a signal responsive to a pressure at an abdominal site of a patient;

at least one electrode, which is adapted to be coupled to an anatomical site of the patient; and a control unit, which is adapted to receive the signal, to analyze a characteristic of the signal so as to identify a voluntary contraction of abdominal musculature of the patient that indicates an onset of a pelvic condition of the patient, and, responsive to analyzing the signal, to apply to the at least one electrode an electrical waveform configured to inhibit the condition.

Preferably, the sensor includes a pressure sensor, and the control unit is adapted to analyze a rate of change of the received signal, and to identify the voluntary contraction responsive to a low rate of change of the received signal.

There is also provided, in accordance with a preferred embodiment of the present invention, a device, including:

at least one electrode, which is adapted to be implanted at a pelvic muscle site of a patient; and a control unit, which is adapted to drive the at least one electrode to apply to the muscle an electrical waveform configured to Inhibit urine retention of the patient.

Typically, but not necessarily, the control unit is adapted to receive an input from the patient and to apply the waveform responsive to the input.

The control unit is preferably adapted to configure the waveform to have (a) a frequency component between about 1 and 10 Hz, (b) an amplitude between about 3 and 9 V, (c) a series of pulses having widths between about 0.05 and 0.2 ms, and/or (d) a duration of about 20—45 seconds.

For some applications, the control unit is adapted to configure the waveform to include a rise time lasting between about 1 second and 5 seconds prior to attaining a designated waveform application voltage. Alternatively or additionally, the control unit is adapted to configure the waveform to include a decay time lasting between about 1 second and 5 seconds prior to returning to a baseline voltage.

The control unit is preferably adapted to configure the waveform to have a duty cycle between about 50% and 100%.

There is further provided, in accordance with a preferred embodiment of the present invention, a method for implanting a medical device in a patient, including:

creating a suprapubic incision in the patient;

creating a vaginal mucosa incision in the patient;

passing between the two incisions an electrode lead which is adapted for coupling to the medical device; and implanting the medical device in the patient.

Preferably, implanting the device includes implanting a device which is capable of treating a stress incontinence condition of the patient, an urge incontinence condition of the patient, an urge frequency condition of the patient, a fecal incontinence condition of the patient, an interstitial cystitis condition of the patient, a chronic pelvic pain condition of the patient, and/or a urine retention condition of the patient.

In a preferred embodiment, passing the electrode lead includes subcutaneously passing an inter-incision introducer between the two incisions, and passing the electrode lead through the introducer. In this case, the method preferably also includes:

removing the inter-incision introducer, so as to leave an end of the electrode lead accessible;

inserting a second introducer into the vaginal mucosa incision, such that a distal end of the second introducer is proximate a urethral sphincter site of the patient;

inserting the end of the electrode lead through the second introducer; and securing the lead to the urethral sphincter site.

The present invention will be more fully understood from the following detailed description of the preferred embodiments thereof, taken together with the drawings, in which:

BRIEF DESCRIPTION OF THE DRAWINGS

FIG. 2I is a schematic, partly sectional illustration showing implantation of the device of FIG. 1A in the pelvis of a patient, in accordance with yet another preferred embodiment of the present invention;

DETAILED DESCRIPTION OF PREFERRED EMBODIMENTS

Figure 1A:
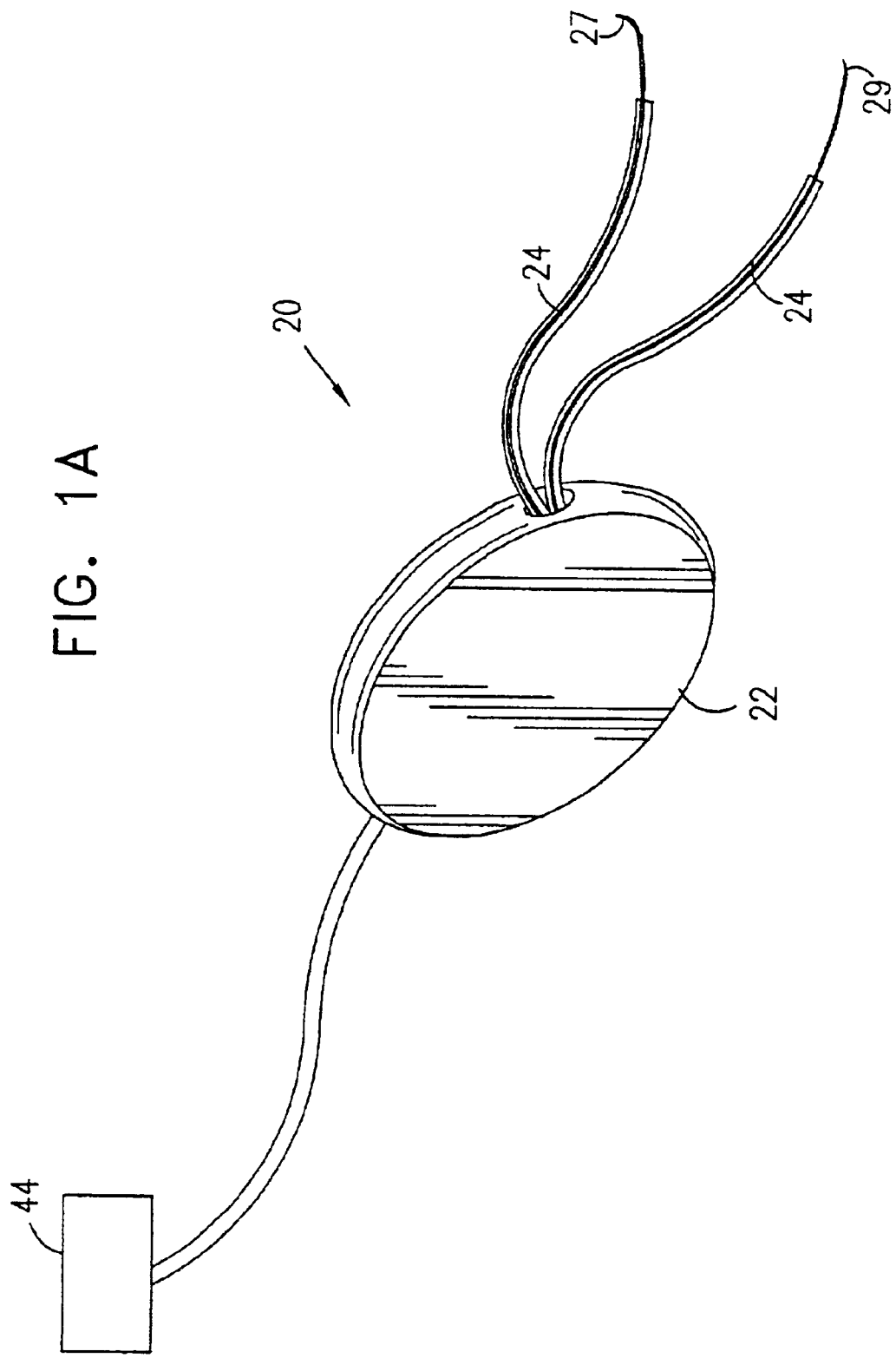
FIG. 1A is a schematic, pictorial view of an implantable device for prevention of mixed incontinence, in accordance with a preferred embodiment of the present invention.

I. Overview of Preferred Embodiments
  A. General description of stimulator device
  B. Sensing and control functions of the device
  C. Signal processing
  D. Power consumption control
II. Detailed Description of Figures
  A. External elements of a stimulator device
  B. Anatomical and surgical considerations
  C. Signal processing
    (i) hardware and algorithms
    (ii) simulation of a typical EMG
    (iii) experimentally measured EMG signals: distinguishing incontinence from voluntary voiding
  D. Muscle stimulation
  E. Provision of power to the control unit
  F. External communication with the control unit
  G. Utilization of other sensors
  H. Reduction of power consumption I. Overview of Preferred Embodiments A. General Description of Stimulator Device Various aspects of the present invention are described in this section (I) and in greater detail in the following section (II). As described with reference to the preferred embodiments shown in FIGS. 1A and 1B, an electronic stimulator device is preferably implanted in the genital region of a patient who has at least two types of incontinence. The device stimulates one or more of the muscles or nerves in the region, so as to control and treat the patient's incontinence. A preferred method for implanting the device is shown in FIGS. 2A, 2B, 2C, 2D, 2E, 2F, and 2G.

Preferably, imminent urge or stress incontinence generates an electromyographic (EMG) signal in the muscles, which is sensed by one or more electrodes and is analyzed by a control unit of the device. Alternatively or additionally, non-electromyographic signals (e.g., pressure signals) are received and analyzed by the control unit. When the control unit determines that the signals are indicative of a condition that is likely to cause involuntary urine flow from the bladder, it applies an electrical waveform to the one or more electrodes, which is configured to treat the particular type of incontinence detected (e.g., stress or urge), in order to stimulate a pelvic muscle to contract and inhibit the urine flow. It is to be understood that although some preferred embodiments of the present invention are described herein with respect to interpreting EMG signals so as to identify the onset of a particular condition, in many of these embodiments, analysis of pressure signals or other non-EMG signals may be performed instead of or in addition to the analysis of the EMG signals.

B. Sensing and Control Functions of the Device

In addition to EMG sensing electrodes, the device preferably also comprises one or more other physiological sensors, described hereinbelow with reference to FIGS. 2H, 2I, 3, 4, 10A, and 10B, which generate signals responsive to, for example, motion, intravesical or abdominal pressure, or urine volume in the bladder. These signals are indicative of some forms of incontinence.

Typically, when the urine volume in the bladder is low, there will be no urine flow even when the abdominal pressure does increase. As described with reference to a plurality of the figures, the control unit preferably processes the signals from the various sensors and uses them to determine when the electrical stimulation should be applied to the muscles.

C. Signal Processing

Figure 7:
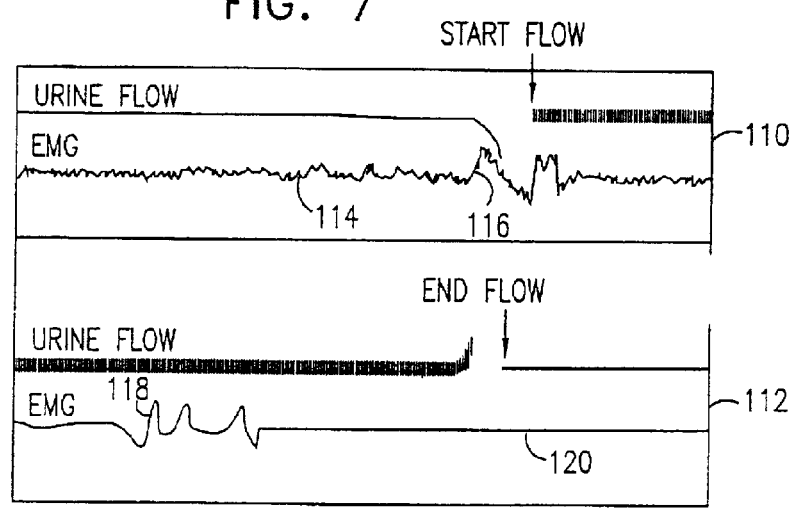

Preferably, the control unit comprises a processor, e.g., as described with reference to FIGS. 3 and 4, which is additionally programmed to distinguish between signals indicative of possible incontinence and other signals that do not warrant stimulation of a nerve or muscle. In particular, the processor is preferably programmed to recognize signal patterns indicative of normal voiding, and does not stimulate the muscles when such patterns occur, so that the patient can pass urine normally. Detection of normal voiding is described in more detail with reference to FIGS. 7 and 8.

Preferably, the processor analyzes both long-term and short-term variations in the signals, as well as rates, spectral patterns, and patterns of change in the signals. For example, to inhibit stress incontinence, the processor may set a threshold of an aspect of the EMG signal that varies over time responsive to an assessment of the patient's physiological condition. Subsequently, the processor applies the stimulation only when a transient variation in the aspect of the EMG signal exceeds the threshold. Methods for modifying the threshold in real time are described with reference to FIG. 6.

In the context of the present patent application and in the claims, a "time-varying threshold" is to be understood as comprising substantially any appropriate time-varying detection parameters that a person skilled in the art, having read the disclosure of the present patent application, would consider useful in applying the principles of the present invention. By way of illustration and not limitation, these time-varying detection parameters may include magnitude, rate, or other aspects of the EMG signal, or of quantitative ultrasound, pressure, or acceleration measurements, as described herein.

D. Power Consumption Control

As described with reference to FIG. 5, the control unit preferably comprises a low-power, low-speed processor, which monitors the EMG and/or sensor signals continuously, and a high-speed processor, which turns on only when the low-speed processor detects an increase in EMG or other activity. Use of the two processors has been shown to significantly reduce consumption of electrical power. The high-speed processor performs an accurate analysis of the signals to determine whether stimulation is actually warranted.

Alternatively or additionally, the concepts described herein with respect to two independent processors may be applied using a single processor having two modes of operation—a low power, low capacity mode, and a high power, high capacity mode.

II. Detailed Description of Figures

A. External Elements of a Stimulator Device

Reference is now made to FIG. 1A, which is a schematic, pictorial illustration of an implantable electronic stimulator device 20, in accordance with a preferred embodiment of the present invention. Device 20 is preferably implanted in the pelvic region of a patient, as described further hereinbelow, for use in providing muscle and/or nerve stimulation so as to control and treat urinary urge and stress incontinence.

Device 20 comprises a control unit 22 and electrodes 27 and 29, coupled thereto by electrical leads 24. Additionally, device 20 preferably comprises at least one additional physiological sensor 44, such as a miniature ultrasound transducer, one or more accelerometers, a pressure transducer or other sensors known in the art.

The control unit preferably comprises circuitry for sensing electrical signals received by electrodes 27 and 29, such as electromyogram (EMG) signals, along with circuitry for processing the signals from sensor 44. Control unit 22 additionally comprises circuitry for applying electrical stimulation waveforms to one or both of the electrodes responsive to the signals. Details of control unit 22 and electrodes 27 and 29 are preferably as described in the above-cited PCT Patent Publications WO 00/19940, entitled "Incontinence Treatment Device," and WO 00/19939, entitled, "Control of urge incontinence," with appropriate changes as described herein or as are otherwise indicated by clinical and engineering considerations that will be clear to those skilled in the art.

The electrodes are preferably flexible intramuscular-type wire electrodes, about 1–5 mm long and 50–100 microns in diameter, thus designed to minimize patient discomfort. They are typically formed in the shape of a spiral or hook, as is known in the art, so that they can be easily and permanently anchored in the muscle. The wire from which the electrodes are made comprises a suitable conductive material, preferably a biocompatible metal such as silver, a platinum/iridium alloy (90/10) or a nickel/chromium alloy. Leads 24 are preferably 5–10 cm long and surrounded by an insulating jacket typically comprising nylon, polyurethane, Teflon or another flexible, biocompatible insulating material. An optional additional wire (not shown) inside the jacket serves as an antenna for the purpose of wireless communications with device 20, as described further hereinbelow.

Control unit 22 preferably comprises circuitry for processing electrical signals received from electrodes 27 and 29 and for applying a waveform to the electrodes. The circuitry is preferably contained in a case made of titanium or other suitable biocompatible metal. Typically, the case is about 20 mm in diameter and 4 mm thick. For some applications, the case serves as a ground electrode for electrodes 27 and 29 when they are sensing or stimulating in a monopolar mode. Alternatively, the case may comprise metal coated with a layer of biocompatible plastic, such as polymethyl methacrylate (PMMA) or silicone. Although two electrodes and one sensor are shown attached to the control unit in FIG. 1A, it is possible to use only a single electrode or, alternatively, additional electrodes and/or other sensors, as described further hereinbelow.

Figure 1B:
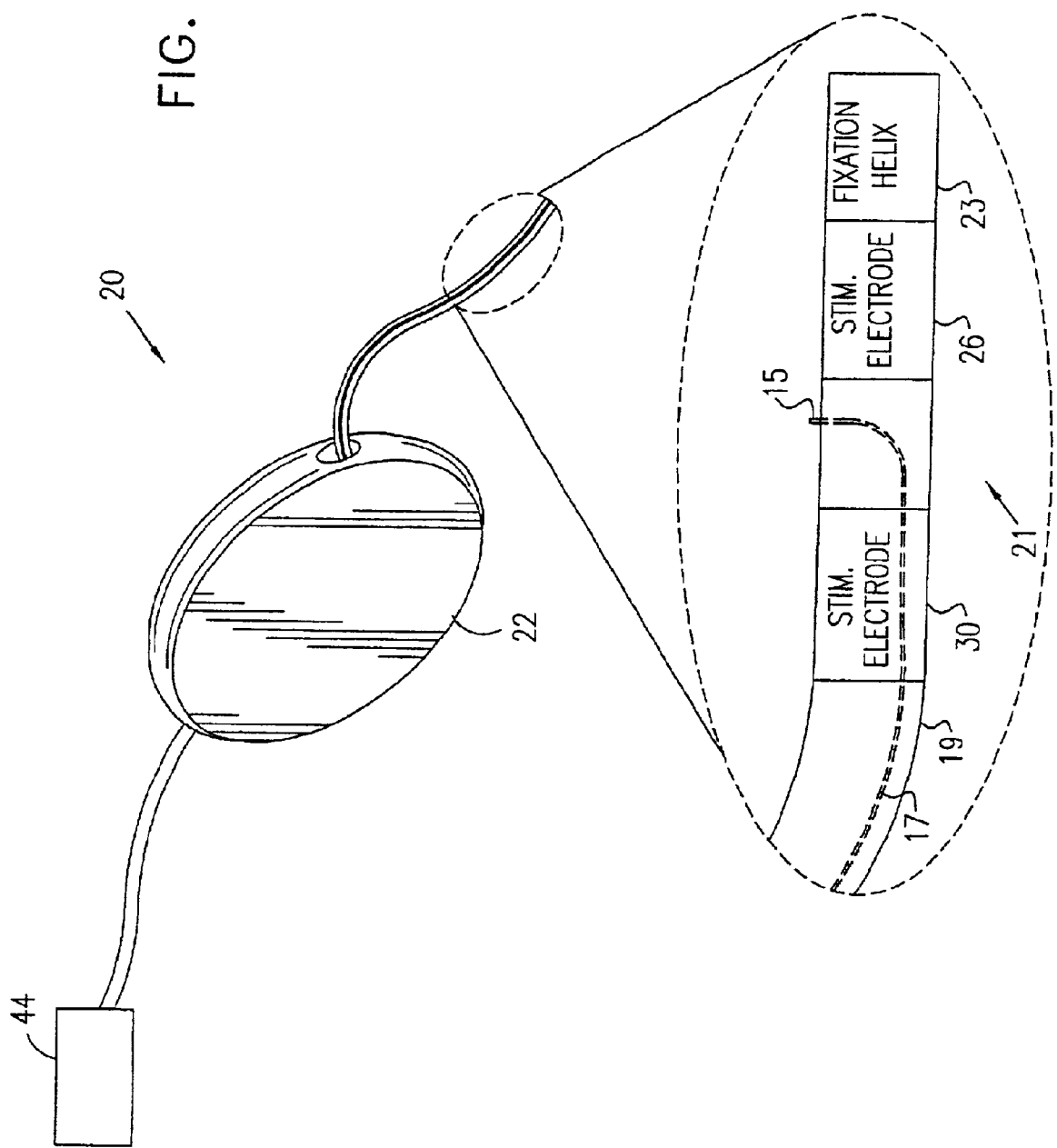
FIG. 1B is a schematic, pictorial view of an implantable device for prevention of mixed incontinence, in accordance with another preferred embodiment of the present invention.

FIG. 1B is a schematic, pictorial illustration of electronic stimulator device 20, in accordance with another preferred embodiment of the present invention. Except with respect to the differences described hereinbelow, the embodiment shown in FIG. 1B is generally similar to the embodiment shown in FIG. 1A, and techniques described herein with respect to one of the configurations can generally be applied to the other configuration, mutatis mutandis.

A lead 21 is preferably provided to couple control unit 22 to a pelvic muscle of the patient. Lead 21 is secured to the muscle by means of a fixation helix 23 or other techniques known in the art, so as to provide electrical contact between the muscle and two stimulation electrodes 26 and 30 disposed on a silicon casing 19 of the lead. Each electrode is typically less than about 80 mm in length, and is most preferably approximately 3 mm in length. The electrodes are typically separated by approximately 3 mm along the length of lead 21. In this space between electrodes 26 and 30, a tip 15 of an EMG wire 17 may protrude approximately 100 microns through casing 19, for those applications in which EMG sensing is desirable. Typically, the diameter of wire 17 is approximately 50 microns, and the diameter of casing 19 is approximately 1.5 mm.

B. Anatomical and Surgical Considerations

FIGS. 2A, 2B, 2C, 2D, 2E, 2F and 2G show a method for implantation of a pelvic stimulation device, in accordance with a preferred embodiment of the present invention. It is emphasized that although this implantation method represents a preferred method, other procedures, including those known in the art, may also be adapted for use with other embodiments of the present invention. For illustrative purposes, the procedure is shown when performed upon a female patient. Unlike many implantation procedures known in the art, the implantation procedure provided by this embodiment is typically performed under local anesthesia, with the patient placed in the lithotomy position. It will be appreciated that the surgical procedure shown in these figures has further benefits over many similar prior art implantation procedures, in that the complication rate resulting therefrom is significantly reduced by virtue of its being carried out in a region substantially devoid of major blood vessels, and in a manner that avoids risk to delicate structures.

Figure 2A:
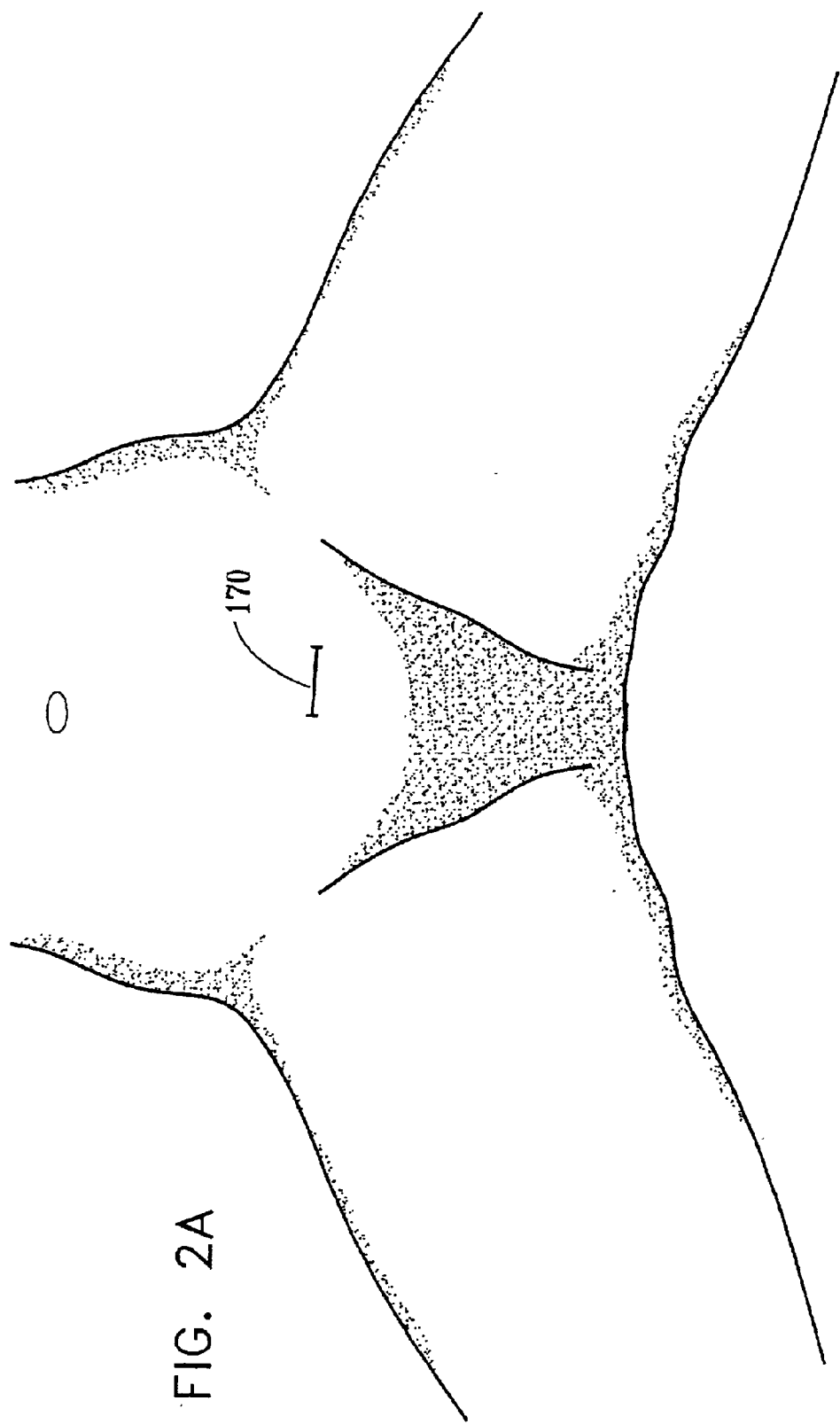
FIGS. 2A, 2B, 2C, 2D, 2E, 2F, and 2G show steps in an implantation procedure of a stimulation device, in accordance with a preferred embodiment of the present invention.

FIG. 2A shows a 4 cm long "pocket" incision 170, made approximately 1 cm cephalad to the pubic bone in order to create a pocket in the subcutaneous tissue adjacent to the fascia. A control unit will later be introduced into this pocket.

Figure 2B:
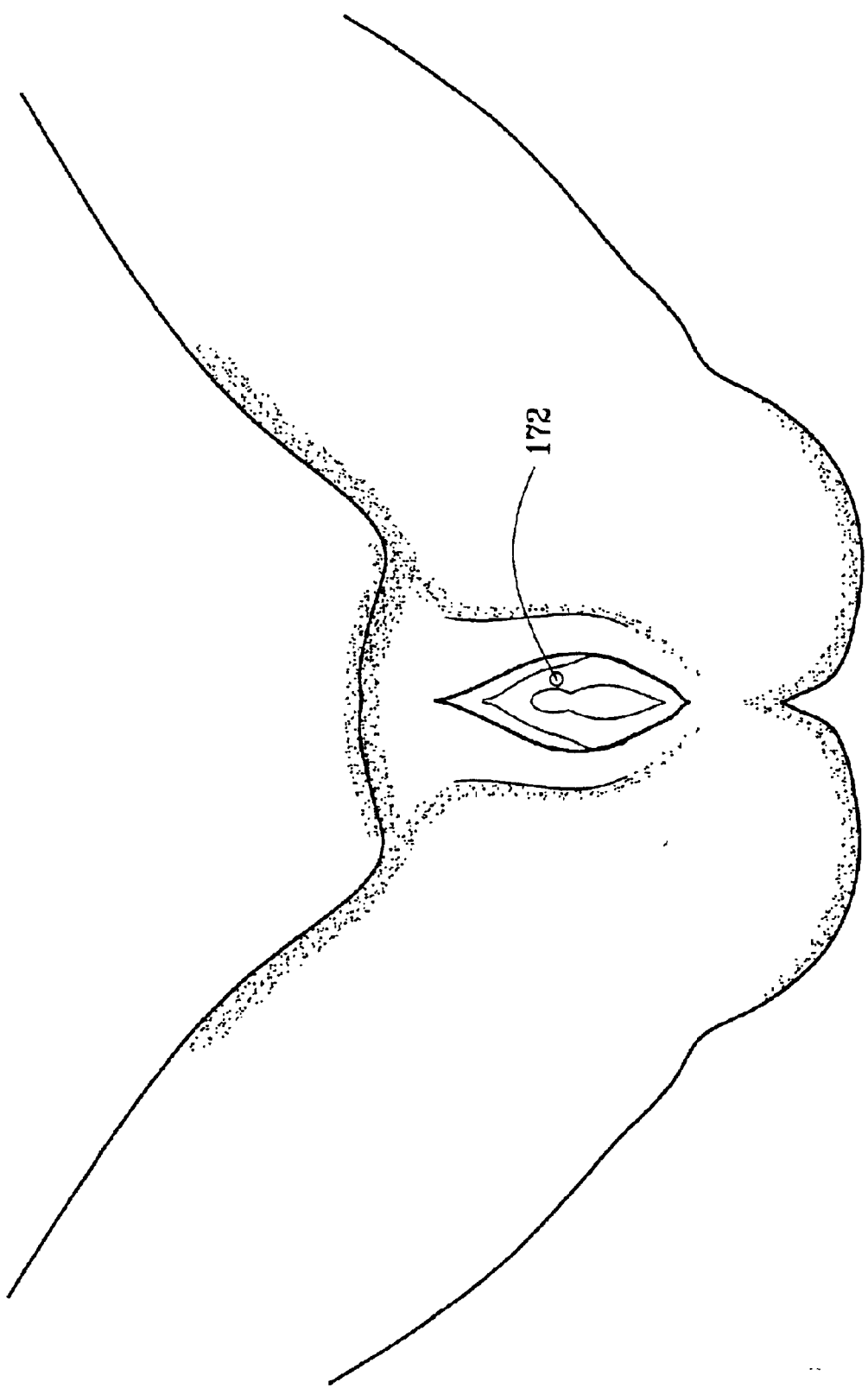

FIG. 2B shows a vaginal mucosa incision 172. This second incision, approximately 0.5–1 cm long, is preferably made through the vaginal mucosa until the subcutaneous tissue, at a site approximately 0.5–1 cm anterior and lateral to the urethral meatus.

Figure 2C:
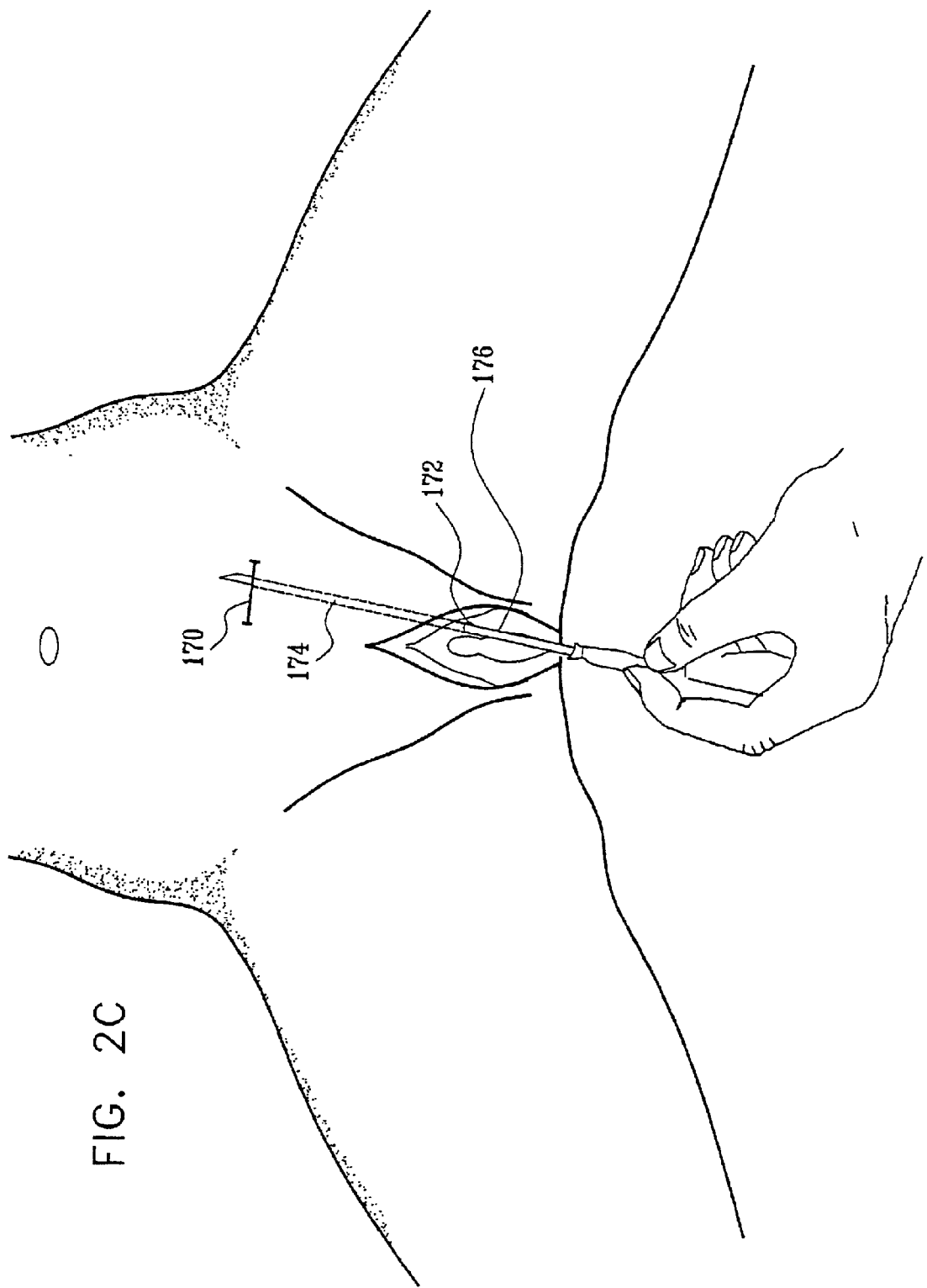

FIG. 2C shows the creation of a subcutaneous tunnel 174 using a 12 Fr introducer 176, placed in incision 172, and conveyed subcutaneously until it reaches and exits through incision 170.

Figure 2D:
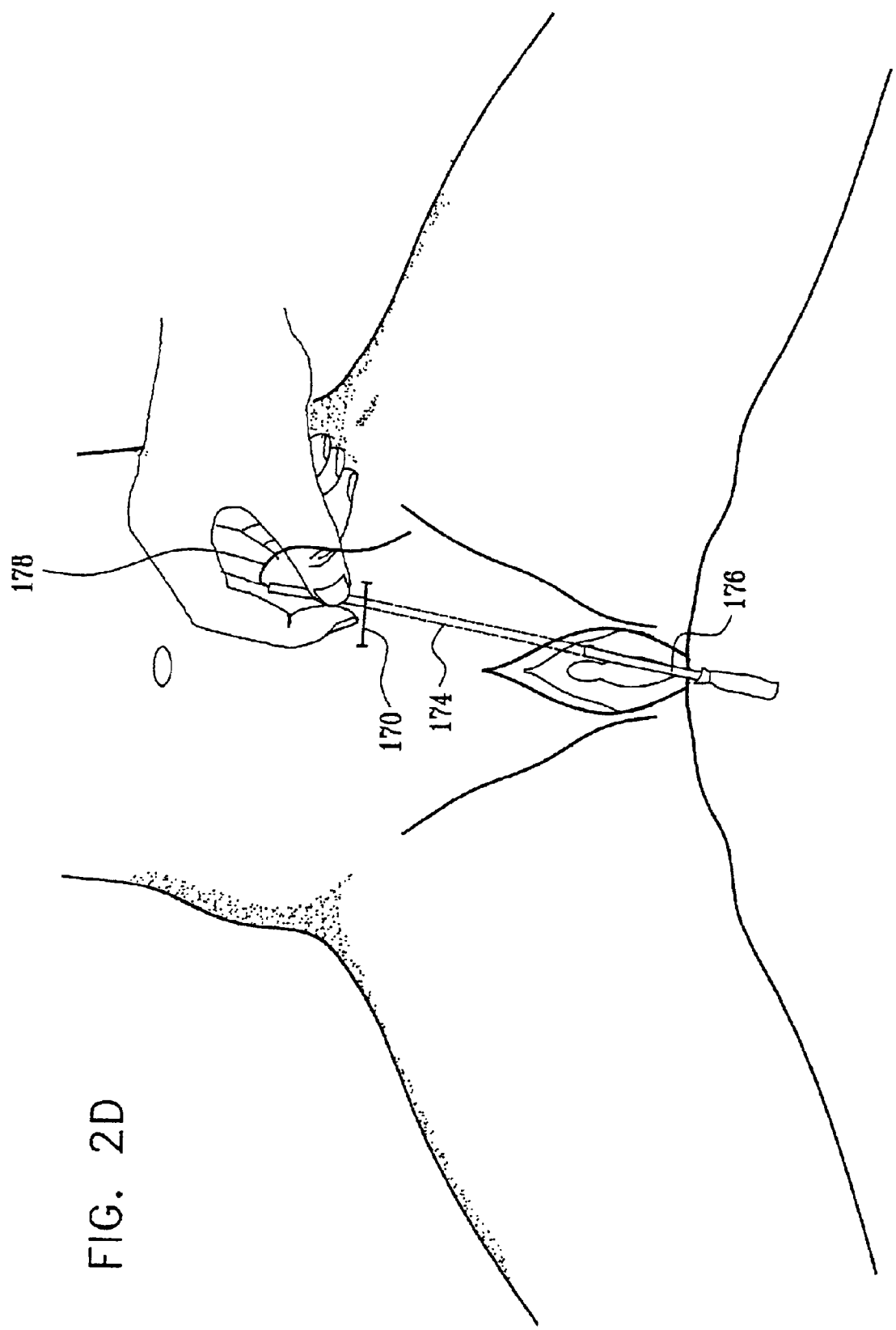

FIG. 2D shows the insertion of a stimulation lead 178 through introducer 176 until its exit at the lower end of the introducer.

Figure 2E:
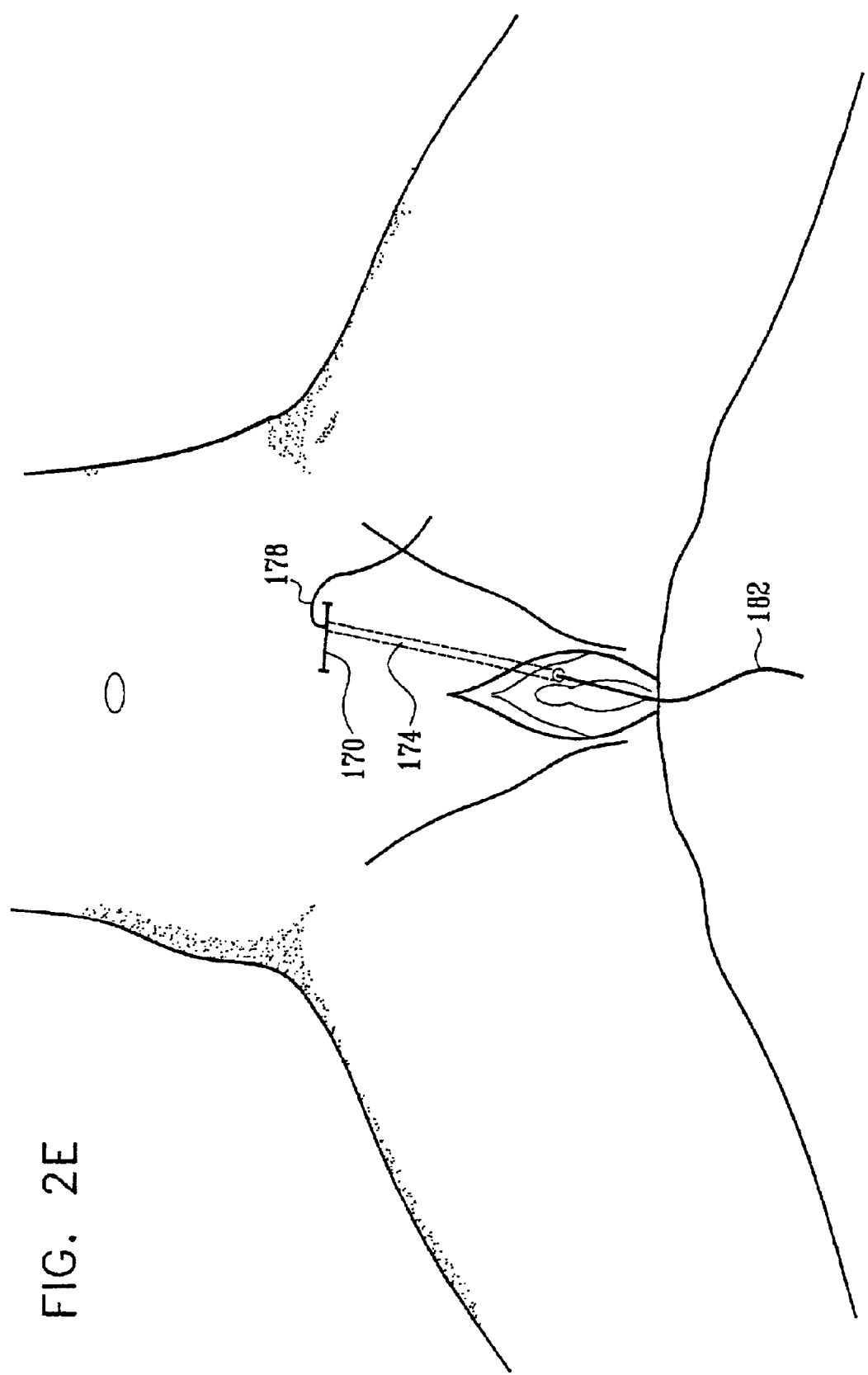

FIG. 2E shows a stimulation lead tip 182 remaining outside incision 172 after the removal of introducer 176.

Figure 2F:
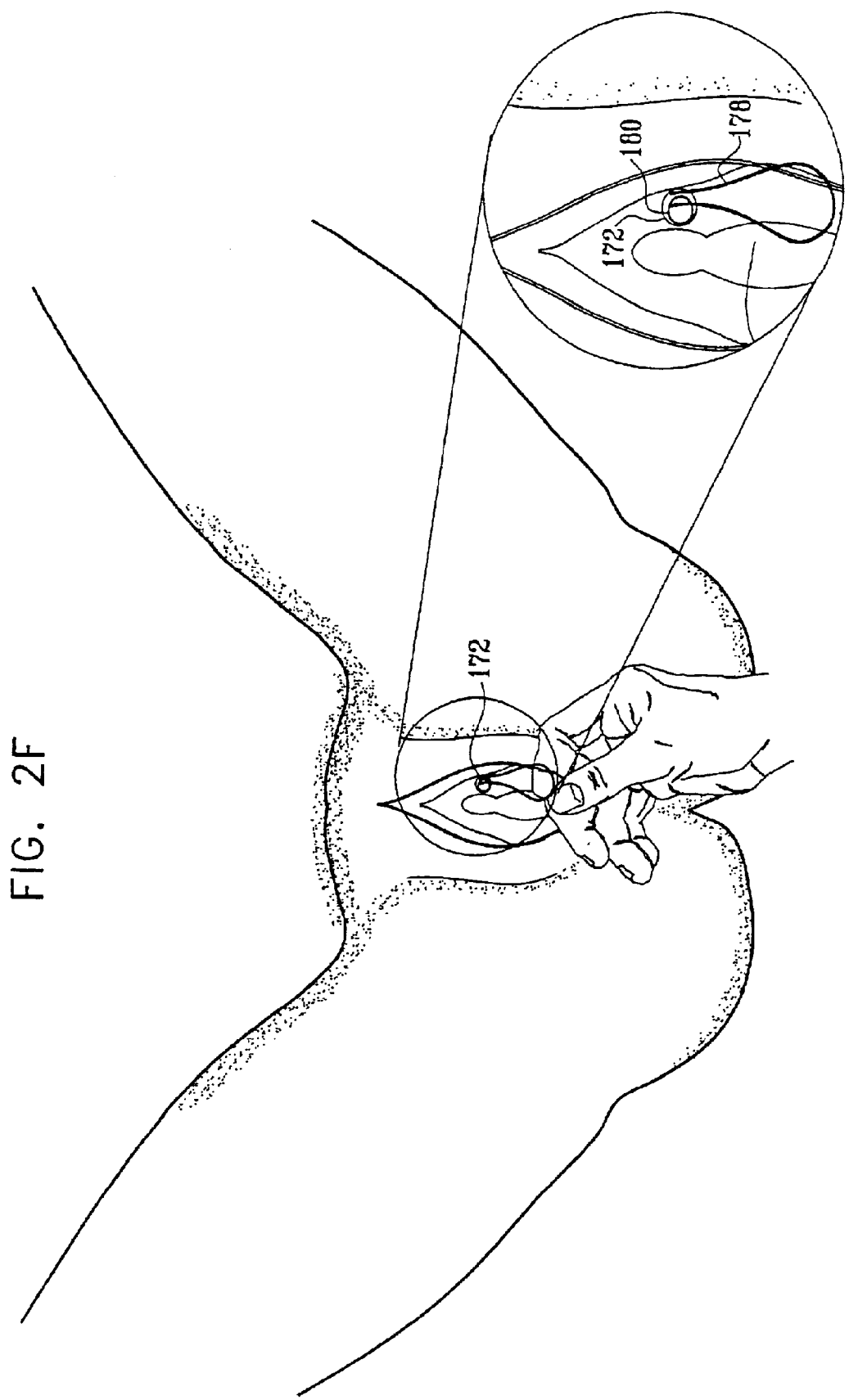

FIG. 2F shows the reinsertion of stimulation lead 178 into incision 172. A 5 Fr splittable short introducer 180 is inserted into incision 172, adjacent to lead 178. The introducer is aimed slightly medially, i.e., towards the urethra, care being taken not to injure the urethra. Introducer 180 is pushed for a distance of approximately 2.5 cm, to a site 0.5–1 cm lateral to the urethral wall. The free end of stimulation lead 178 is reinserted and advanced through short introducer 180 into the urethral sphincter. Once the stimulation lead is properly secured, introducer 180 is withdrawn by being split into two parts. A 3/0 nylon suture is made in the subcutaneous tissue around the stimulation lead. Subsequently, the free electrode lead is buried subcutaneously, and incision 172 is closed by a 3/0 plain catgut or Dexon suture.

An 8 Fr introducer (not shown) is inserted through incision 170, between the fascia and muscle tissue, so as to reach the retropubic space. A sensor lead (not shown) for a pressure or electrical sensor is advanced through the introducer to a desired position, e.g., in the retropubic space or between fascia and muscle. Following placement of the lead, it is secured to the fascia by a 3/0 nylon suture. Once the sensor has been properly secured, the lead stylet is withdrawn from the introducer, and the introducer is then removed. Connectors for the sensor lead are connected to appropriate sites on the control unit.

Figure 2G:
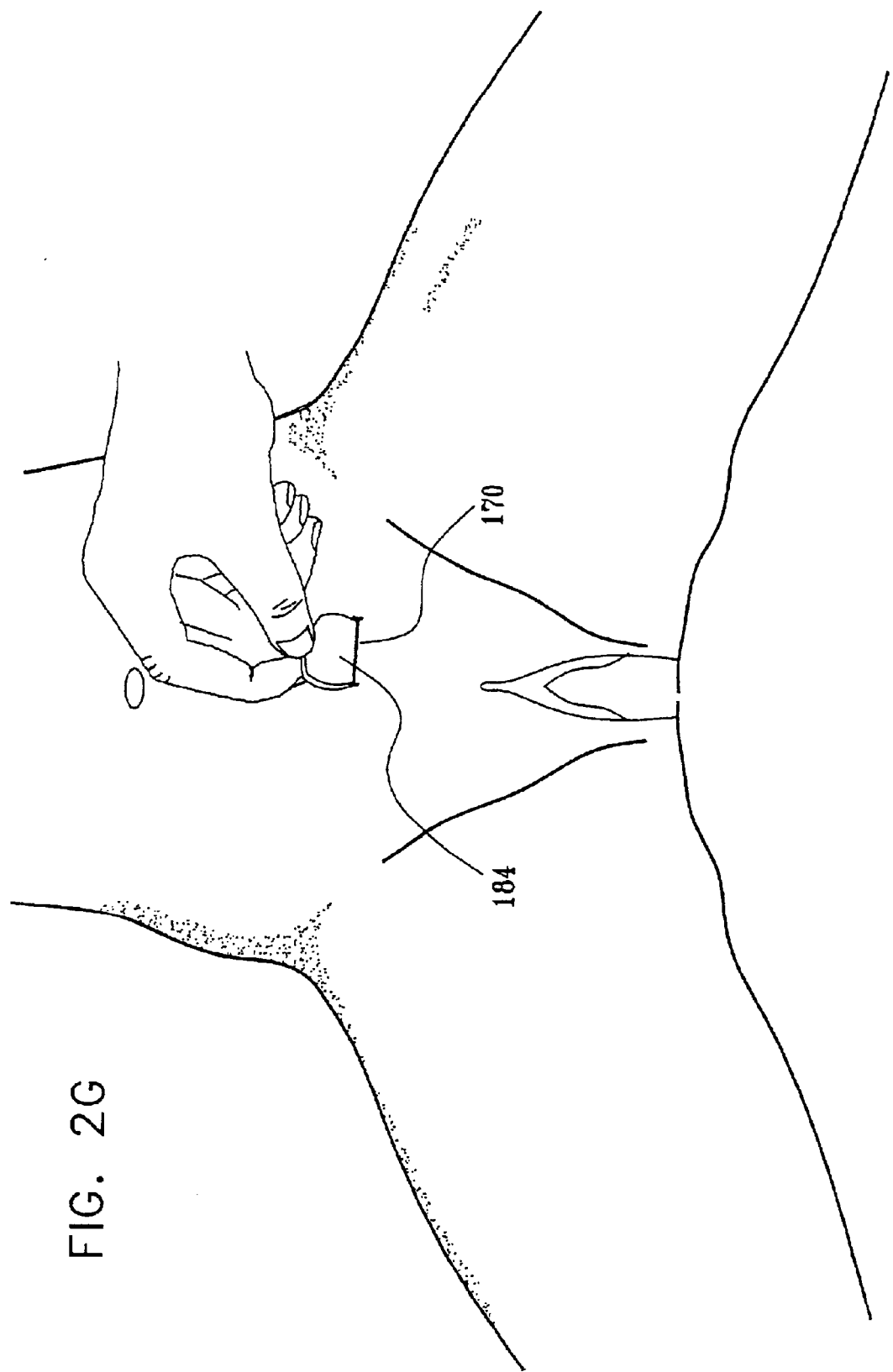

FIG. 2G shows the insertion of a control unit 184 through incision 170. After initial verification of the performance of the implanted system, incision 170 is closed with two layers.

Figure 2H:
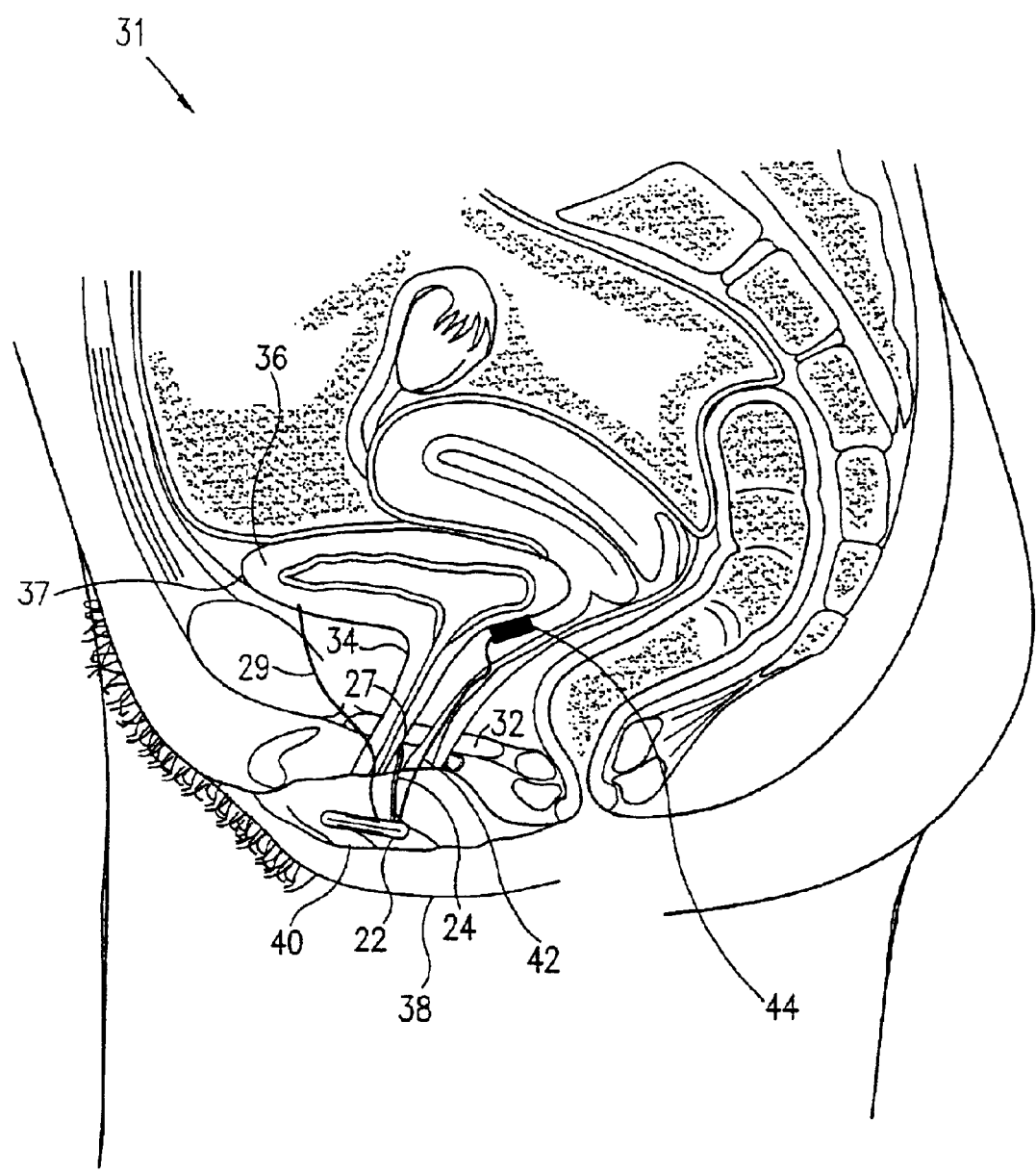
FIG. 2H is a schematic, partly sectional illustration showing implantation of the device of FIG. 1A in the pelvis of a patient, in accordance with another preferred embodiment of the present invention.
Figure 21:
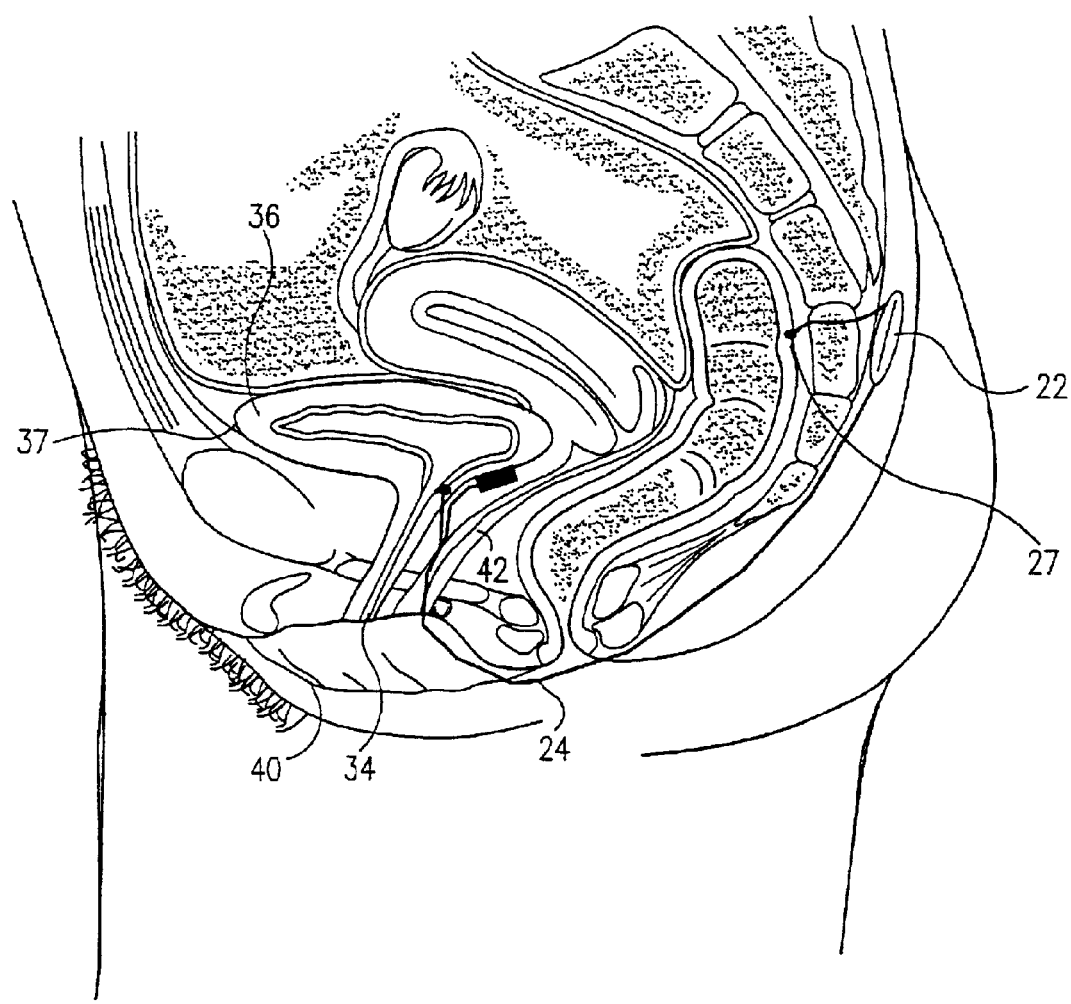

FIG. 2H is a schematic, partly sectional illustration showing the genitourinary anatomy of a female patient 31 in whom device 20 is implanted, in accordance with another preferred embodiment of the present invention. It will be understood that, with appropriate changes, device 20 may be implanted in or coupled to a male patient. In this embodiment, electrode 27 is inserted into a muscle 32, such as the levator ani muscle, in a vicinity of urethra 34 and bladder 36. Electrode 29 is inserted into the patient's detrusor muscle 37, which surrounds bladder 36. Alternatively or additionally, electrodes 27 and 29, or additional electrodes not shown in the figure, may be placed in or adjacent to other muscles of the pelvic floor.

The precise placement of the electrodes is typically not essential, particularly since electrical signals tend to pass among the different muscles in the region. Thus, any placement of the electrode in or on one or more of the pelvic muscles suitable for exercising urine control is considered to be within the scope of this embodiment of the present invention. The electrodes are preferably inserted through an incision made in the wall of vagina 42. Alternatively, another suitable approach may be chosen for ease of access and minimization of tissue trauma.

Control unit 22 is preferably implanted under the skin in the genitopelvic region of patient 31. Most preferably, the control unit is implanted inside the patient's labia minora 38 or in the labia majora 40. Alternatively, the control unit is not implanted in the patient's body, but is instead maintained outside the body, connected by leads 24 to the electrodes. This configuration is convenient particularly for an initial test period, during which the effectiveness of device 20 in treating a given patient is evaluated before permanent implantation.

FIG. 2I is a schematic, partly sectional illustration showing the genitourinary anatomy of patient 31 in whom device 20 is implanted, in accordance with yet another preferred embodiment of the present invention. Preferably, control unit 22 is implanted in a vicinity of the sacral spine, as shown, but may alternatively be implanted in the abdomen or in the pelvis. According to this embodiment, the control unit drives electrode 27 to stimulate a nerve that innervates one or more muscles which are responsible for urine control. Typically, a sacral nerve is stimulated, so as to control the flow of urine from the bladder.

Generally, the choice of implantation location for the control unit, as well as which particular nerve is to be stimulated, is made by the patient's physician, responsive to the patient's condition and other surgical considerations. Preferably, electrode 29 (FIG. 2H), is implanted in the detrusor muscle or in another pelvic muscle, and detects EMG signals, which are conveyed for analysis by the control unit. Alternatively or additionally, bladder pressure and volume sensors (not shown) and electrode 29 convey signals to the control unit responsive to bladder contractions associated with imminent incontinence, whereupon the control unit: (a) analyzes the signals to distinguish between aspects thereof indicative of stress incontinence and aspects thereof indicative of urge incontinence, and (b) drives electrode 27 to stimulate the sacral nerve and/or drives electrode 29 to stimulate the pelvic muscle, using stimulation parameters appropriate for treating the identified form of urinary incontinence.

C. Signal Processing (i) Hardware and Algorithms

Figure 3:
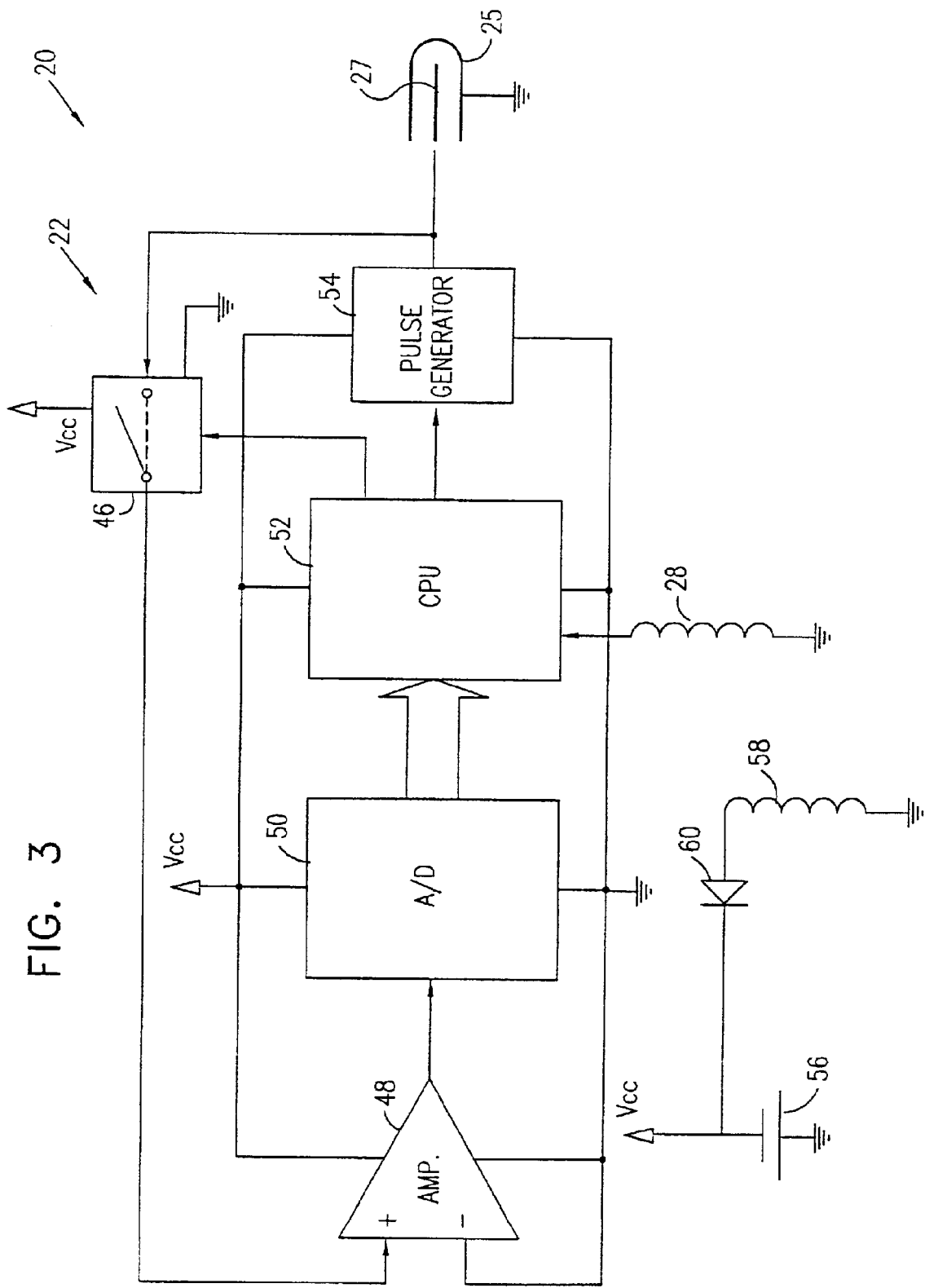
FIG. 3 is a schematic block diagram illustrating circuitry used in an implantable muscle stimulation device, in accordance with a preferred embodiment of the present invention.

FIG. 3 is a schematic block diagram showing circuitry used in control unit 22 to receive signals from and apply electrical waveforms to electrode 27, in accordance with a preferred embodiment of the present invention. Although in this embodiment device 20 is described as operating in a monopolar mode, the principles described hereinbelow are applicable to bipolar operation as well, in which both electrodes 27 and 29 are active.

Electrode 27 receives EMG signals from muscle 32, which are conveyed via a normally-closed switch 46 to the input of an amplifier 48, preferably a low-noise operational amplifier. Amplified signals output from amplifier 48 are digitized by an analog/digital (A/D) converter 50 and conveyed to a central processing unit (CPU) 52, preferably a microprocessor. Preferably, although not necessarily, the amplified signals are not rectified prior to being digitized, to allow various forms of analysis, for example, spectral analysis, to be performed on the raw data, without the distortion imparted by rectification. CPU 52 preferably analyzes these signals and/or signals from other physiological sensors, such as ultrasound, pressure, strain, and acceleration sensors described hereinbelow, to determine whether they fit a pattern indicating that incontinence is likely to result, and, if so, to determine the type of incontinence. The analysis preferably comprises a spectral analysis and an analysis of EMG signal magnitude and rate. Responsive to a determination that a particular form of incontinence is likely, a pulse generator 54 conveys electrical pulses to electrode 27, as described hereinbelow.

Optionally, sensor 44 (FIGS. 1A and 1B) comprises a miniaturized ultrasound transducer, which is implanted in proximity to bladder 36. Additionally or alternatively, sensor 44 comprises a pressure sensor filled with silicon oil, as shown schematically in FIG. 1A. Further alternatively or additionally, sensor 44 comprises a pressure sensor in the bladder, bladder wall, or elsewhere in the abdominal cavity; a strain sensor sutured to the bladder wall; or a sensor which detects action potentials in the bladder muscle. Most preferably, sensor 44 comprises each of these. Signals from the transducer or sensor are conveyed to control unit 22 for analysis, particularly so as to enable the control unit to estimate the urine volume within the bladder. When the bladder is relatively empty, there is no need to actuate electrodes 27 and 29, even when a transient increase in the electromyogram (EMG) signal or another signal would otherwise indicate an increased probability of imminent incontinence. Alternatively or additionally, the EMG signal itself may be analyzed to gain an indication of the urine volume in the bladder, since when the bladder is full, the average EMG activity typically increases. Further alternatively or additionally, analysis such as that described hereinbelow with reference to FIG. 9 may be carried out, typically so as to determine the likelihood of imminent urge incontinence.

The CPU is preferably programmed to distinguish between incontinence-related patterns and other signal patterns not associated with incontinence, such as signals generated when patient 31 wishes to pass urine voluntarily.

Preferably, the CPU gathers long-term statistical information regarding the EMG and the signals from the other sensors, and analyzes the information to "learn" common signal patterns that are characteristic of patient 31. The learned patterns are used in refining decision criteria used by the CPU in determining whether or not to apply waveforms to the electrodes. For some applications, a handheld controller (not shown) receives an input from the patient whenever urine is unintentionally passed, and control unit 22 modifies signal analysis parameters and/or stimulation parameters responsive thereto, so as to reduce the likelihood of future incontinence.

(ii) Simulation of a Typical EMG

Figure 6:
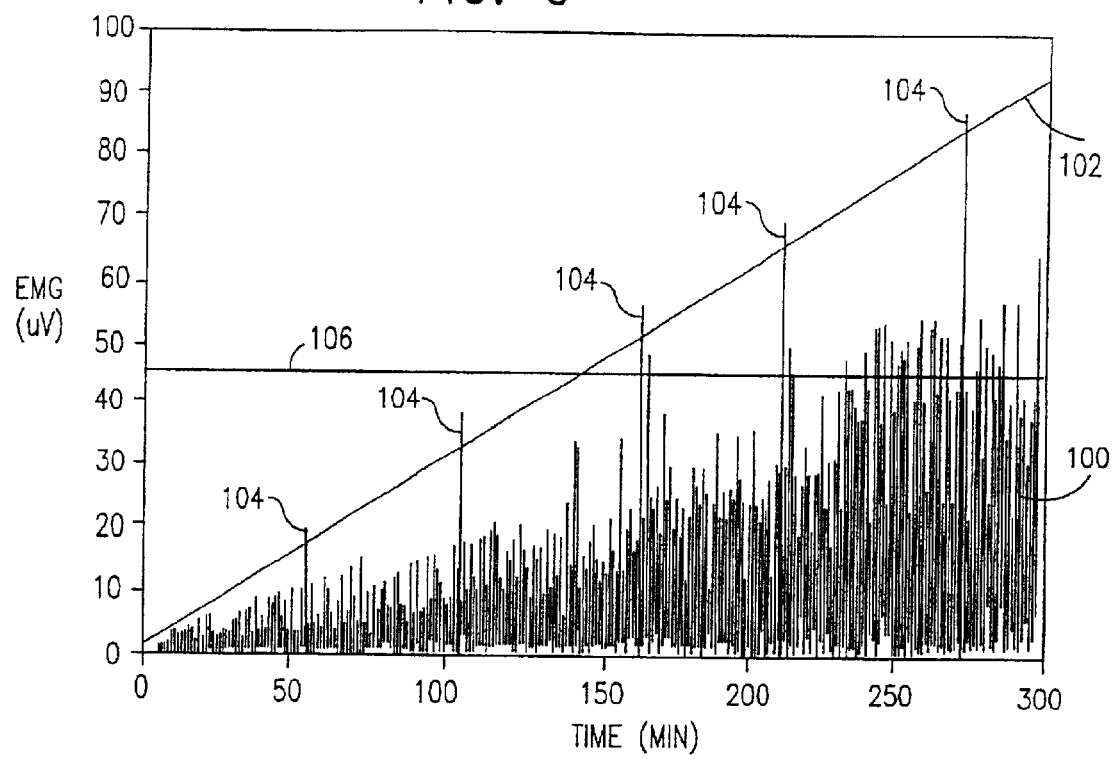
FIGS. 6–9 are graphs showing simulated and measured signals, representative of different aspects of use of an implantable muscle stimulation device, in accordance with a preferred embodiment of the present invention.

FIG. 6 is a graph that schematically illustrates results of a simulation experiment, in accordance with a preferred embodiment of the present invention, including a simulated EMG signal 100 of a woman suffering from stress incontinence. A variable, adaptive threshold level 102 is marked on the graph. Over the course of several hours, as the woman's bladder fill level increases, the average level of EMG signal 100 increases accordingly. In this example, threshold level 102 is computed so as to increase as a function of the average EMG. Alternatively or additionally, threshold level 102 and a plurality of other time-varying detection parameters are calculated as functions of other features of the EMG signal or of other aspects of the woman's condition (particularly as measured by sensors 44, 76 and 78 (FIG. 4)), and are used separately or in combination in determining whether to apply stimulation to inhibit involuntary urine flow. As shown, adaptive threshold level 102 enables five possible incidents of incontinence, marked by excursions 104 of signal 100 over level 102, to be detected reliably, with a low false alarm rate. On the other hand, if a fixed threshold level 106 is used, as is known in the art, some EMG excursions 104 are missed (at t=60 and 110 minutes), and, moreover, the false alarm rate is high (at t>220 minutes).

(iii) Experimentally Measured EMG Signals: Distinguishing Incontinence from Voluntary Voiding FIG. 7 includes graphs 110 and 112 that schematically illustrate experimental measurements made before, during and after voluntary voiding of urine, in accordance with a preferred embodiment of the present invention. Graph 112 is a continuation in time of graph 110. The upper trace in both graphs illustrates urine flow, wherein the beginning and end of voluntary flow are marked by arrows. The lower trace illustrates measured EMG signals.

In a period preceding voiding, an EMG signal 114 shows substantial high-frequency activity, which is generally indicative of a full bladder. High-frequency spikes in signal 114 (of which none appear in FIG. 7) would be interpreted by CPU 52 as signs of imminent incontinence, leading to actuation of pulse generator 54. On the other hand, voluntary voiding is preceded by a portion 116 of the EMG signal, in which there is a large but gradual increase in the signal level. EMG signal portion 116 is associated with voluntary activation of the pelvic floor muscles for the purpose of passing urine from the bladder, as is a later signal portion 118 during the same act of voiding. Therefore, CPU 52 preferably analyzes not only the level of the EMG signals, but also a rate of change of the signals, in order to distinguish between voluntary and involuntary contractions of the pelvic muscles. When the rate of change is characteristic of voluntary voiding, no stimulation is applied by pulse generator 54.

Figure 8:
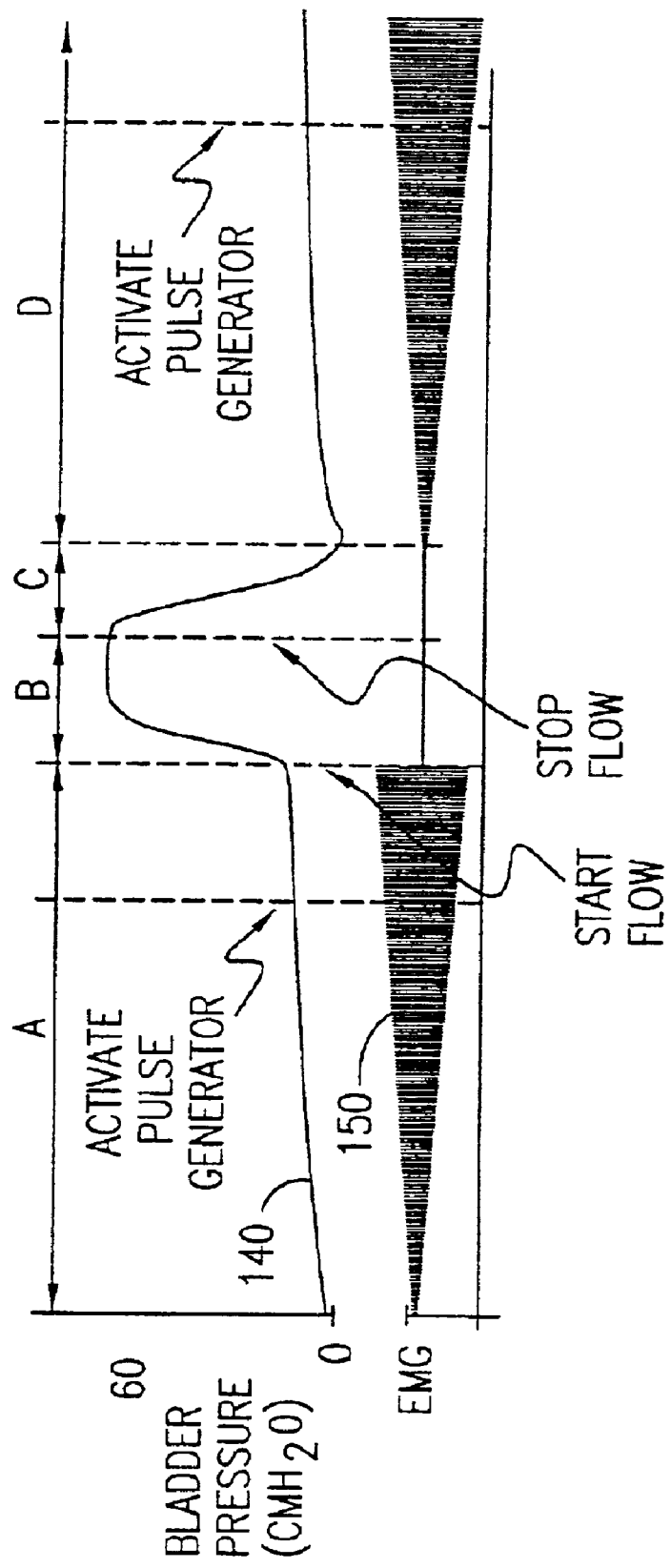

FIG. 8 (not to scale) includes two graphs, showing: (a) data recorded during a series of periods A, B, C and D, representing stages before, during, and after urination, and (b) preferred times with respect to these periods for activation of pulse generator 54 in order to inhibit urge incontinence, in accordance with a preferred embodiment of the present invention. Bladder pressure data 140 and EMG data 150 shown in FIG. 8 are based on text and a figure in the above-referenced book, *Urinary Incontinence* (p. 35), which describes the voluntary voiding of a healthy adult human female subject. Preferably, inputs to control unit 22 include the EMG data and bladder pressure data, to enable the control unit to determine an appropriate time to activate the pulse generator.

During period A, the bladder fills, which filling is preferably detected and identified as such by the control unit. Notably, in period A there is a slow, steady increase in bladder pressure, as well as a slow, steady increase in peak-to-peak amplitude of the EMG signal. Bladder pressure is seen to increase sharply during voiding period B, in comparison to the slow increase of period A. During period C, voiding was terminated. During period D, the bladder fills again, in substantially the same manner as in period A. Examination of periods B and C shows that the EMG signal has essentially zero magnitude during voiding and during its termination, and generally increases with increasing bladder pressure during the bladder-filling periods A and D.

Preferably, control unit 22 identifies an initiation time of normal voiding by analysis of the EMG and/or bladder pressure data. In a preferred embodiment, the control unit actuates pulse generator 54 to apply pulses to electrodes 27 and/or 29 at a predetermined time after voiding. For example, in an interview conducted during the calibration period, it may be determined that a particular patient generally only experiences urge incontinence greater than 1.5 hours following voluntary voiding. The control unit may then be programmed to detect voiding and initiate pulse application one hour thereafter, and to continue the pulse application until a subsequent onset of voluntary voiding is detected.

Alternatively or additionally, the pulse generator may be actuated by the control unit when the average magnitude of the EMG exceeds a specified threshold, because the likelihood of urge incontinence reflects the increased bladder pressure indicated by the EMG signal exceeding the threshold. Further alternatively or additionally, the calibration period may include a training period, in which the control unit continually samples the EMG signal, and in which the patient indicates to the control unit whenever urge incontinence occurs. During or subsequent to the training period, the control unit or an external processor (not shown) analyzes each instance of urge incontinence to determine aspects of the EMG and/or other sensor signals preceding the incontinence which can be used during regular operation of the unit to predict incontinence. For many applications of the present invention, the control unit is operative to execute some or all of the above methods, so as to minimize or eliminate occurrences of urge incontinence. It will be appreciated that these strategies may be applied to other types of incontinence as well, mutatis mutandis.

Figure 9:
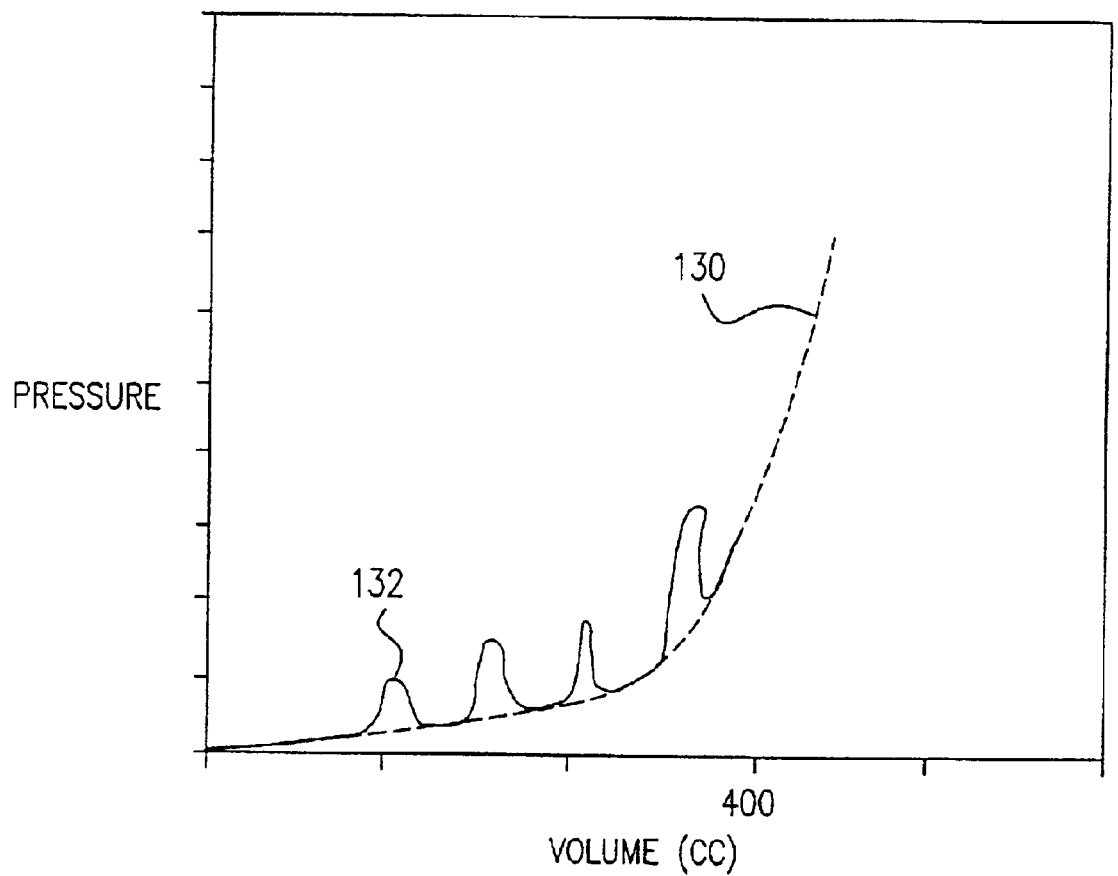

FIG. 9 is a graph showing simulated data, for use in detecting the imminent onset of urge incontinence, in accordance with a preferred embodiment of the present invention. Preferably, control unit 22 analyzes a measured pressure-volume (or pressure-time) relationship of the patient's bladder, so as to determine whether the pressure is increasing in a healthy manner, as represented by dashed line 130, or whether it is characterized by one or more relatively sharp features 132, which may indicate detrusor instability and imminent urge incontinence. Preferably, if urge incontinence is deemed likely, then control unit 22 initiates the stimulation of a pelvic muscle using protocols appropriate for treating the urge incontinence (described hereinbelow), which are typically different from those suitable for the treatment of stress incontinence. Measurement of bladder volume may be performed using ultrasound techniques or by means of a strain gauge fixed to the patient's bladder. It is to be understood that whereas a pressure-volume curve is shown in FIG. 9, a pressure-time curve may similarly be generated and subsequently interpreted to identify analogous sharp features indicative of imminent urge incontinence.

Alternatively or additionally, the patient is enabled to instruct control unit 22 to initiate electrical stimulation of the muscles in order to inhibit urge incontinence which the patient senses may be imminent. For example, the patient may input the instruction to the control unit by voluntarily tightening her abdominal muscles, which in turn causes measurable increases in abdominal pressure. Advantageously, the rate of increase of abdominal pressure generated by voluntary contraction of the abdominal musculature is significantly smaller than that increase generated involuntarily, for example, during laughter. Typically, the patient can be taught in a single training session to generate a detectable and distinguishable muscle contraction, appropriate for controlling device 20. For some applications, control unit 22 comprises an external input unit, such as a keypad with buttons designated for certain functions, e.g., "Inhibit urge incontinence now," or "Inhibit stress incontinence now."

In a preferred embodiment, stress incontinence and urge incontinence are distinguished solely (or at least in part) responsive to differences in d(Pressure)/dt characteristic of the respective conditions. For example, values of dP/dt greater than a threshold value are interpreted as being indicative of stress incontinence, while values of dP/dt less than the threshold are interpreted as being indicative of urge incontinence.

D. Muscle Stimulation

With reference to FIG. 3, when possible stress incontinence is detected, CPU 52 opens switch 46 and drives pulse generator 54 to apply a suitable electrical waveform to electrode 27 so as to stimulate muscle 32 to contract and thereby inhibit the incontinence which was detected. Switch 46 is opened in order to avoid feedback of the stimulation waveform to amplifier 48, and is closed again after the waveform is terminated. In the embodiment shown in FIG. 3, the waveform is applied to the electrode in a monopolar mode, whereby a case 25 of control unit 22 serves as the return (ground) electrode. (This mode can be used only when case 25 comprises a conductive material. When control unit 22 has a plastic case, at least two electrodes on one or more leads are generally needed, in order to administer bipolar stimulation.)

For some applications, as muscle 32 contracts, it closes off urethra 34, thus inhibiting the undesired urine flow. Preferably, the waveform is terminated and switch 46 is closed after a predetermined period of time has passed, e.g., 0.5–1 second to treat stress incontinence and 10 minutes to treat urge incontinence. Alternatively or additionally, the waveform is terminated and switch 46 is closed if the patient voids voluntarily or other new data indicate that the expected incontinence is no longer likely. If possible incontinence is again detected at this point, the waveform is re-applied.

It will be appreciated that, depending on the particular application, one or more waveforms may be employed in the practice of various embodiments of the present invention. For example, the waveform may be monophasic or biphasic and may have a range of amplitudes, duty cycles and/or frequencies. It has been found generally that pulse frequencies in the range between 2 and 50 Hz are effective in engendering contraction of the levator ani and other pelvic muscles, but for some applications it may be appropriate to use frequencies outside of this range. Certain preferred stimulation parameters are described hereinbelow.

Preferably, but not necessarily, the same electrode or electrodes are used to treat both stress incontinence and urge incontinence; however, different stimulation parameters are utilized depending on the particular form of incontinence which is immediately to be treated. Alternatively, at least one electrode is dedicated to treating a particular form of incontinence, e.g., an electrode implanted so as to stimulate the sacral nerve may be driven by control unit 22 to apply current most suitable for treating urge incontinence.

As described hereinabove, the processor preferably identifies the form of incontinence based on particular physiological characteristics detected by the sensors, and control unit 22 applies an appropriate stimulation signal responsive thereto. For example, stress incontinence may be detected using techniques described hereinabove with reference to FIGS. 6 and 7, and urge incontinence may be detected using techniques described with reference to FIGS. 8 and 9. In patients with mixed incontinence, these techniques are typically sufficient to reveal the significant differences between the two types of incontinence, e.g., the impulsive pressure and/or EMG spikes in instances of stress incontinence are generally not present in urge incontinence, while the pressure-volume and pressure-time features characteristic of detrusor instability and urge incontinence are correspondingly not characteristic of stress incontinence.

For some applications, two sensors are implanted at different sites within the patient. These generate signals which, in combination, are analyzed by control unit 22 so as to determine whether a stress incontinence event or an urge incontinence event is imminent. In a preferred configuration, one pressure sensor is coupled to measure intravesical pressure, while another pressure sensor is coupled to measure intra-abdominal pressure. Sharp increases in bladder pressure that occur generally simultaneously with sharp increases in overall abdominal pressure are typically interpreted to be indicative of possible imminent stress incontinence, e.g., due to laughter. By contrast, increases in bladder pressure that are not accompanied by increases in overall abdominal pressure are interpreted as being indicative of imminent urge incontinence.

Responsive to a determination of imminent incontinence, and the identification of the particular type of incontinence, the stimulation waveform is preferably applied, typically comprising a bipolar square wave having characteristics summarized in Table I. This table also indicates appropriate stimulation parameters for the treatment of other disorders, such as fecal incontinence, interstitial cystitis (IC), chronic pelvic pain, and urine retention, described hereinbelow. For some applications and some patients, other parameters may also be used.

TABLE I

|  | Stress and fecal incon. | Urge event | Chronic pelvic pain and IC | Urine retention |
| --- | --- | --- | --- | --- |
| Amp. | 3–9 V | 0.5–5 V | 1–4 V | 3–9 V |
| Freq. | 40–50 Hz | 5–15 Hz | 5–15 Hz | 1–10 Hz |
| Pulse width | 0.05–1 ms | 0.05–1 ms | 0.05–0.2 ms | 0.05–0.2 ms |
| Duration of signal | 0.2–1 s (stress); 1–20 s (fecal incon.) | 5–10 min | 10–30 min | 20–45 s |
| Rise time to peak amp. | ~0 | 0–1 min | 0–3 min | 0–5 s |
| Decay time | ~0 | 0–1 min | 0–3 min | 0–5 s |
| Optional bursts (Duty cycle) | Bursts not used. | 1–5 s on, 20–60 s off. Typical duty | 2 s on, 20 s off. Typical duty cycle: 5- | 5–10 s on, 5–10 s off. Typical duty |

TABLE I-continued

| Stress and fecal incon. | Urge event | Chronic pelvic pain and IC | Urine retention |
|---|---|---|---|
| | cycle: 5-15% | 15% | cycle: 50-100% |

Thus, it is seen that in response to a determination of imminent stress incontinence, e.g., due to the patient sneezing, a high-power waveform is applied, typically having both a high amplitude and a high frequency. This form of stimulation is generally preferred in inhibiting the rapid onset of stress incontinence, as the stimulation develops significant muscular contraction over a very short time period, so as to prevent the involuntary passing of urine. Shortly after the triggering event (e.g., the sneeze) has finished, the stimulation is preferably removed, because the likelihood of imminent incontinence is diminished.

By contrast, imminent urge incontinence is typically more suitably treated over a longer time period. For example, a signal may be applied from the time that control unit 22 determines that urge incontinence is imminent until the control unit determines that the patient has voluntarily voided. Because of the nature of urge incontinence, i.e., it is characterized by the involuntary and undesired contraction of bladder muscles, a lower energy waveform is applied to a spinal site and/or to a pelvic floor muscle. This lower energy waveform is preferably configured to induce a relaxation response of the muscle tissue of the bladder, and to thereby inhibit involuntary urination. Advantageously, since the treatment of urge incontinence typically does not consume electrical power at the same rate as the treatment of stress incontinence, the drain on implanted batteries resulting from the treatment of urge incontinence is typically low, allowing the appropriate waveforms to be applied for significantly longer time periods than those useful for treating stress incontinence.

For some applications, the waveform for treating urge incontinence is applied in bursts, e.g., the waveform is applied for about 1–5 seconds, and then removed for about 20–60 seconds. Typically, the relatively short bursts are sufficient to provide the patient with protection against incontinence during the inter-burst periods. Advantageously, such a protocol of waveforms in bursts further reduces the consumption of electricity.

In a preferred embodiment, for example, when treating patients with severe urge incontinence, it is beneficial to treat the urge incontinence prophylactically, i.e., more frequently than when a particular event of urge incontinence is imminent. In this embodiment, waveforms are typically applied automatically, at a fixed time after voluntary voiding and/or whenever bladder volume or pressure exceeds a threshold. Alternatively or additionally, for some patients, the treatment for urge incontinence is applied substantially continuously. Preferably, but not necessarily, these continuous or very-frequent modes of treatment are applied in bursts, as described hereinabove.

For some urge incontinence treatment applications, it is beneficial to extend the initiation of the application of the waveform over a period ranging from several seconds to about one minute. Thus, for example, a 10 Hz square wave may be increased to a designated waveform application voltage of 2 V over a period of 2 seconds, which is generally fast enough to inhibit urge incontinence, without inadvertently providing a sharp stimulus that might elicit unintentional voiding. When it is desired to apply the waveform in intermittent bursts, the amplitude is typically held at the peak value for approximately 1–5 seconds, and subsequently caused to decay over a period of several seconds. An extended decay time is also believed by the inventors to inhibit inadvertently eliciting the sharp bladder contractions which in some instances may bring about incontinence.

Although preferred embodiments of the present invention are generally described herein with respect to control unit 22 distinguishing between stress incontinence and urge incontinence, and applying an appropriate treatment responsive thereto, it is to be understood that other disorders may also be treated some of the techniques described herein, mutatis mutandis. Thus, for example, chronic pelvic pain and interstitial cystitis are preferably treated using stimulation parameters shown in Table I. As in the treatment of stress or urge incontinence, the patient herself is typically enabled to activate control unit 22 to treat the condition. Alternatively or additionally, the control unit is programmed to apply an appropriate waveform responsive to a determination of bladder volume (e.g., via an ultrasound measurement), bladder pressure, and/or based on the time from last voiding. Voiding is preferably determined using techniques described herein, such as measuring changes in abdominal pressure, or analyzing pelvic floor EMG data. Typically, interstitial cystitis and chronic pelvic pain are treated, like urge incontinence, using electric signal application parameters configured to induce relaxation of the bladder.

As shown in Table I, pathological retention of urine (a condition common in patients with paraplegia) is preferably treated by the application to a pelvic floor muscle of a waveform configured to facilitate voiding. Preferably, the patient is enabled to enter a command into an external controller whenever voiding is desired.

In a preferred embodiment of the present invention, fecal incontinence is treated by the application of a waveform to a pelvic floor site or to a site in or adjacent to the anal sphincter of the patient. Typically, waveform parameters are generally similar to those for treating stress incontinence. Additionally, because fecal incontinence often accompanies urinary incontinence, particularly stress incontinence, the same techniques described herein for detecting the onset of stress incontinence (e.g., EMG or pressure measurements) are preferably adapted for use in detecting the onset of fecal incontinence.

In normal physiological functioning, an accumulation of feces in the rectum causes afferent signaling that leads to involuntary smooth muscle contraction in the pelvic region and to voluntary contraction of the striated muscle of the anal sphincter. These contractions of smooth and striated muscle provide the control required to defer defecation until a desired time. For some patients, fecal incontinence is caused at least in part by an impairment of the afferent signaling which should occur responsive to an accumulation of feces.

Therefore, in a preferred embodiment of the present invention, control unit 22 is adapted to enhance the functioning of this afferent pathway, in order to restore normal levels of smooth and/or striated muscle contractions, and, consequently, to restore fecal continence. Preferably, control unit 22 senses the pressure in the patient's rectum, or senses another parameter indicative of rectal filling, and drives electrodes implanted in or near the patient's anal sphincter to apply a signal which generates (or amplifies) afferent signaling. Typically, this induced afferent signaling is sufficient to alert the patient to the gradually increasing level of rectal filling, such that the patient will naturally respond by tightening the striated muscle of the anal sphincter. Often, the induced sensation is indistinguishable from analogous natural sensations experienced by healthy individuals.

Advantageously, smooth muscle contractions are also believed to occur responsive to the induced afferent signaling, such that after a period of weeks to several months, smooth muscle contractions are expected to supplement the striated muscle contractions, and provide enhanced protection against fecal incontinence.

For some applications, the magnitude, frequency, and/or duty cycle of the applied signal is configured to simulate the body's natural afferent signaling patterns, i.e., to have lower values when the rectum is only slightly full, and to increase in value responsive to indications of increased rectal filling.

It is to be appreciated that preferred stimulation parameters are described herein by way of illustration and not limitation, and that the scope of the present invention includes the use of waveforms comprising, for example, biphasic and/or monophasic components, a decaying square wave, a sinusoid or sawtooth waveform, or any other shape known in the art to be suitable for stimulating muscle or nervous tissue. Generally, appropriate waveforms and parameters thereof are determined during an initial test period of device 20, and are updated intermittently, either in a healthcare facility or automatically during regular use.

E. Provision of Power to the Control Unit

Figure 4:
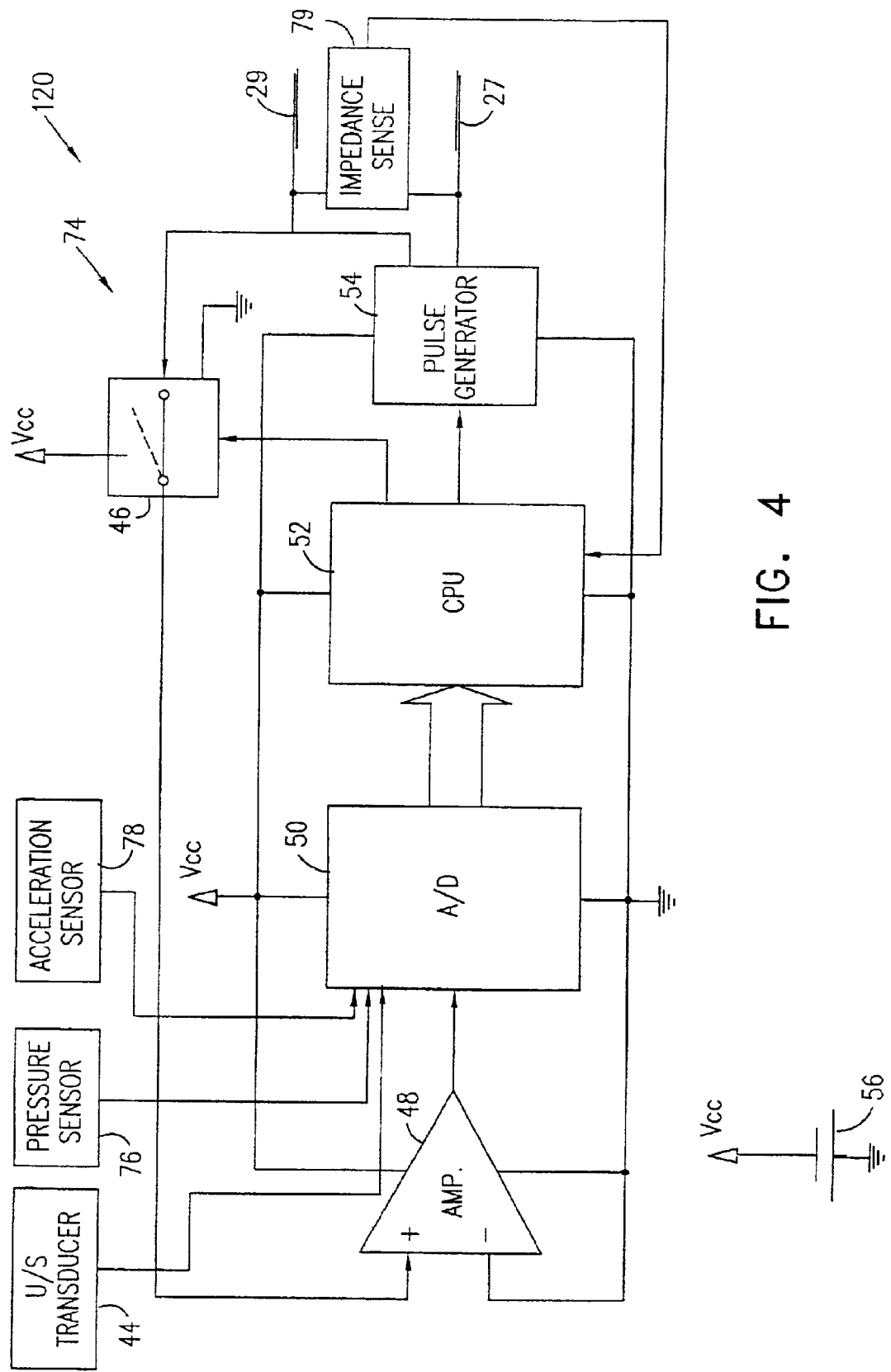
FIG. 4 is a schematic block diagram illustrating circuitry used in an implantable muscle stimulation device, in accordance with another preferred embodiment of the present invention.

With reference to FIGS. 3 and 4, power is supplied to the elements of control unit 22 by a battery 56, which may comprise a primary battery (non-rechargeable) and/or a rechargeable battery. Alternatively, a super-capacitor, as is known in the art, may be used to store and provide the electrical power. If a rechargeable battery or super-capacitor is used, it is preferably recharged via an inductive coil 58 or antenna, which receives energy by magnetic induction from an external magnetic field charging source (not shown) held in proximity to the pelvis of patient 31. The magnetic field causes a current to flow in coil 58, which is rectified by a rectifier 60 and furnished to charge battery 56. An optional coil 28, coupled to CPU 52 for the purpose of wireless communications with device 20, may also be used for charging the battery.

Preferably, battery 56 comprises a standard battery, such as a lithium battery, having a nominal output of 3 volts. Most preferably, pulse generator 54 comprises a DC/DC converter, as is known in the art, and a capacitor, which is charged by the DC/DC converter to a constant, stepped-up voltage level regardless of the precise battery voltage, which may vary between 3.5 and 1.8 volts. The same DC/DC converter, or another similar device, preferably supplies power to other circuit components of control unit 22.

F. External Communication with the Control Unit

An inductive arrangement using coil 28 is preferably used to program the CPU, using an external programming device (not shown) with a suitable antenna. Alternatively, the programming device generates a modulated magnetic field to communicate with a receiver inside case 25, which preferably senses the field using a Hall effect transducer. Such programming may be used, for example, to set an amplitude or duration of the stimulation waveform applied by pulse generator 54, or to set a threshold level or other parameters, according to which the CPU distinguishes between electromyographic or other signals that are indicative of impending urge or stress incontinence and those that are not (e.g., those that indicate voluntary voiding). Such programming may be carried out by medical personnel or by the patient herself, who can similarly turn the implanted control unit on and off as desired by passing a suitable magnet over her pelvis.

Although the circuit blocks in control unit 22 are shown as discrete elements, some or all of these blocks are preferably embodied in a custom or semi-custom integrated circuit device, as is known in the art.

G. Utilization of other Sensors

FIG. 4 is a schematic block diagram illustrating a muscle stimulator device 120, in accordance with an alternative embodiment of the present invention. Device 120 is substantially similar to device 20, except for features described hereinbelow. Device 120 comprises a control unit 74, which is coupled to electrodes 27 and 29. Electrode 29 also serves as a sensing electrode, furnishing electromyographic signals via switch 46 to amplifier 48, as described hereinabove. Alternatively, electrodes 27 and 29 may be coupled as differential inputs to amplifier 48. Pulse generator 54 applies the stimulation waveforms between electrodes 27 and 29 in a bipolar mode.

In addition to or instead of the electromyographic signals received from electrode 29, CPU 52 preferably receives additional signals from other physiological sensors, such as an ultrasound transducer, a pressure sensor 76 and/or an acceleration sensor 78, or other types of strain and motion measurement devices, as are known in the art. Pressure sensor 76 is preferably implanted on or in bladder 36, so as to detect increases in abdominal or intravesical pressure that may lead to involuntary urine loss. Similarly, acceleration sensor 78 is preferably implanted so as to detect bladder motion associated with hypermobility, which is similarly associated with urine loss. The additional signals from these sensors are preferably analyzed by the CPU together with the electromyographic signals in order to improve the accuracy and reliability of detection of impending incontinence.

An impedance sensor 79 is preferably used to measure the tissue impedance between leads 27 and 29, using physiological impedance measurement techniques known in the art. During long-term use of device 120 (or other such devices), fibrosis in the area of the implanted electrodes tends to cause the impedance to increase, so that the stimulating current for a given applied voltage decreases. The impedance measured by sensor 79 is used as a feedback signal instructing CPU 52 to increase the voltage, so that a generally constant level of stimulation current is maintained.

Figure 10A:
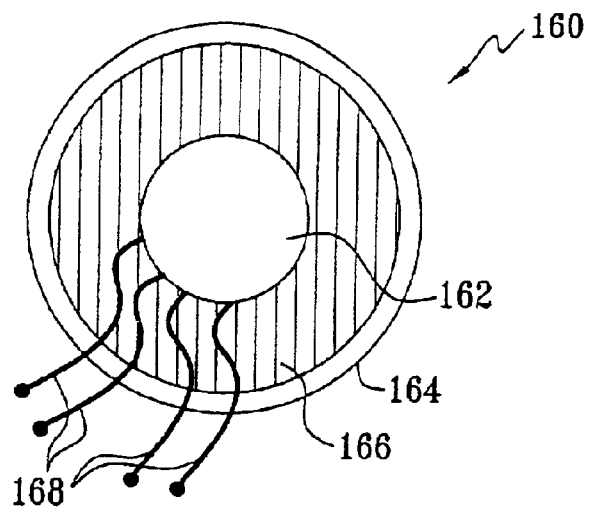
FIG. 10A is a schematic diagram of a pressure sensor, in accordance with a preferred embodiment of the present invention.

FIG. 10A is a schematic illustration (not to scale) showing details of a sensor 160 for measuring intravesical pressure, in accordance with a preferred embodiment of the present invention. Sensor 160 preferably comprises a pressure-sensitive element such as a piezoelectric element or a piezoresistive element 162. Element 162 is typically surrounded by silicon oil 166 or a similar liquid, which, in turn, is contained within a flexible wall 164. Preferably, element 162 is connected by four leads 168 to control unit 22. Leads 168 are preferably coupled in a Wheatstone bridge formation, such that pressure on wall 164 induces a change in resistance of piezoresistive element 162 which, in turn, is detected by control unit 22. Typically, control unit 22 applies a voltage across two of the leads, and senses and amplifies the voltage developed across the other two leads in order to ascertain the pressure being applied to sensor 160. In order to increase battery life, the voltage applied across the leads is preferably applied in short pulses (e.g., 50 microseconds on, 30 milliseconds off).

Figure 10B:
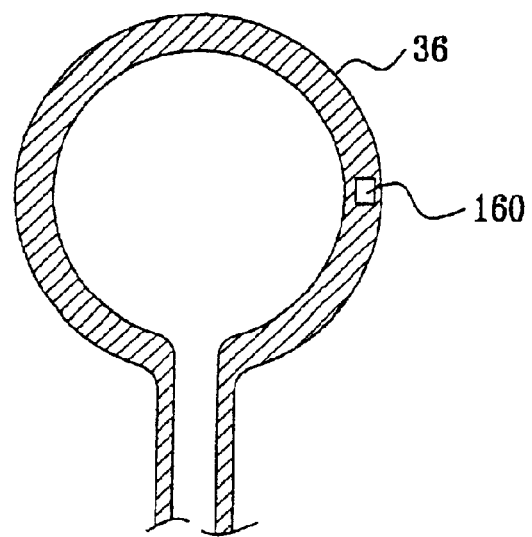
FIG. 10B is a schematic, sectional illustration of the bladder of a patient, showing implantation therein of the pressure sensor of FIG. 10A, in accordance with a preferred embodiment of the present invention.

FIG. 10B is a schematic illustration (not to scale) showing sensor 160 implanted in the muscle wall of bladder 36, in accordance with a preferred embodiment of the present invention. Typically, one or more sensors 160 are implanted in or on the bladder wall or elsewhere in the abdominal cavity.

H. Reduction of Power Consumption

Figure 5:
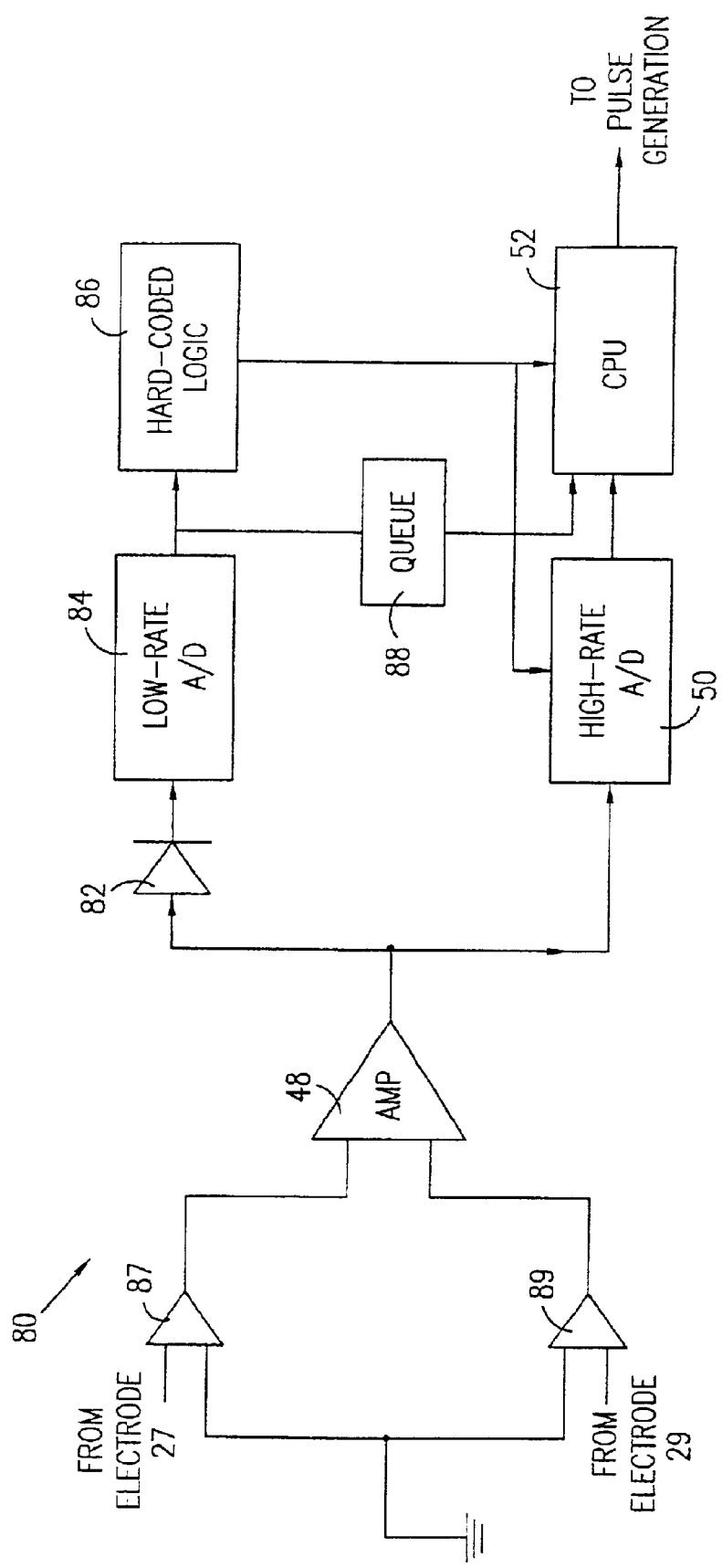
FIG. 5 is a schematic block diagram illustrating signal processing circuitry for analyzing electromyogram signals, in accordance with a preferred embodiment of the present invention.

FIG. 5 is a schematic block diagram showing details of signal processing circuitry 80 for use in device 20 or 120, in accordance with a preferred embodiment of the present invention. In order to detect impending incontinence with adequate reliability, A/D converter 50 optimally samples the EMG signals from the electrodes at 1000–5000 Hz, and CPU 52 preferably performs a detailed analysis of the sample stream. Systems for incontinence control known in the art, operating at sample rates below 1000 Hz, cannot adequately distinguish between signals that may be indicative of incontinence and those that are not. For the purpose of such high-rate sampling, CPU 52 preferably comprises a low-power, software-programmable processor. If A/D converter 50 and CPU 52 were to operate continuously, however, battery 56 would rapidly run down. Therefore, circuitry 80 comprises a low-power, low-resolution A/D converter 84 and hard-coded processing logic 86, which operate continuously at a low sampling rate, preferably at about 100–200 Hz. Input from amplifier 48 to A/D converter 84 is preferably rectified by a rectifier 82.

In operation, A/D converter 50 and CPU 52 are normally maintained in a standby state, in which their power consumption is negligible. When logic 86, operating at the low sampling rate, detects EMG signals that may be a precursor to incontinence, it signals A/D converter 50 to begin sampling at the high rate. In order not to lose significant data from the brief period before A/D converter 50 and CPU 52 turn on, signals from A/D converter 84 are preferably stored in a cyclic (or first-in first-out) queue 88, such as a delay line. The entire sequence of signal detection and processing is estimated to take between 5 and 20 ms, up to the point at which CPU 52 reaches a decision as to whether or not to actuate pulse generator 54. Pulse generation takes between 1 and 20 ms, with the result that contraction of the pelvic muscles begins within 15–50 ms of an onset of increased EMG activity indicating impending urine loss. Thus, urethra 34 is substantially closed off before any significant amount of urine can leak out.

As shown in FIG. 5, EMG inputs from electrodes 27 and 29 are preferably amplified before processing in a dual-differential configuration, so as to afford enhanced sensitivity and reduced noise. Electrodes 27 and 29 are coupled to respective differential preamplifiers 87 and 89, the outputs of which are differentially amplified by amplifier 48.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

What is claimed is:

1. A method for implanting a medical device in a patient, comprising:

creating a suprapubic incision in the patient;

creating a vaginal mucosa incision in the patient;

passing between the two incisions an electrode lead which is adapted for coupling to the medical device; and implanting the medical device in the patient, wherein implanting the device comprises implanting a device which is capable of treating an interstitial cystitis condition of the patient.

2. A method according to claim 1, wherein passing the electrode lead comprises subcutaneously passing an inter-incision introducer between the two incisions, and passing the electrode lead through the introducer.

3. A method according to claim 1, and comprising:

removing the inter-incision introducer, so as to leave an end of the electrode lead accessible;

inserting a second introducer into the vaginal mucosa incision, such that a distal end of the second introducer is proximate a urethral sphincter site of the patient;

inserting the end of the electrode lead through the second introducer; and securing the lead to the urethral sphincter site.

4. A method for implanting a medical device in a patient, comprising:

creating a suprapubic incision in the patient;

creating a vaginal mucosa incision in the patient;

passing between the two incisions an electrode lead which is adapted for coupling to the medical device, wherein passing the electrode lead comprises subcutaneously passing an inter-incision introducer between the two incisions, and passing the electrode lead through the introducer;

implanting the medical device in the patient;

removing the inter-incision introducer, so as to leave an end of the electrode lead accessible;

inserting a second introducer into the vaginal mucosa incision, such that a distal end of the second introducer is proximate a urethral sphincter site of the patient;

inserting the end of the electrode lead through the second introducer; and securing the lead to the urethral sphincter site.

5. A method according to claim 4, wherein implanting the device comprises implanting a device which is capable of treating a stress incontinence condition of the patient.

6. A method according to claim 4, wherein implanting the device comprises implanting a device which is capable of treating an urge incontinence condition of the patient.

7. A method according to claim 4, wherein implanting the device comprises implanting a device which is capable of treating an urge frequency condition of the patient.

8. A method according to claim 4, wherein implanting the device comprises implanting a device which is capable of treating a fecal incontinence condition of the patient.

9. A method according to claim 4, wherein implanting the device comprises implanting a device which is capable of treating a chronic pelvic pain condition of the patient.

10. A method according to claim 4, wherein implanting the device comprises implanting a device which is capable of treating a urine retention condition of the patient.

11. A method according to claim 4, wherein passing the electrode lead comprises subcutaneously passing an inter-incision introducer between the two incisions, and passing the electrode lead through the introducer.

* * * * *